(12) United States Patent
Takama et al.

(10) Patent No.: US 12,337,090 B2
(45) Date of Patent: Jun. 24, 2025

(54) METHOD FOR MANUFACTURING OXYGENATOR

(71) Applicant: TERUMO KABUSHIKI KAISHA, Tokyo (JP)

(72) Inventors: Renjo Takama, Kanagawa (JP); Takeshi Sato, Kanagawa (JP)

(73) Assignee: Terumo Kabushiki Kaisha, Tokyo (JP)

(*) Notice: Subject to any disclaimer, the term of this patent is extended or adjusted under 35 U.S.C. 154(b) by 359 days.

(21) Appl. No.: 17/882,940

(22) Filed: Aug. 8, 2022

(65) Prior Publication Data

US 2022/0378996 A1 Dec. 1, 2022

Related U.S. Application Data

(63) Continuation of application No. PCT/JP2021/006775, filed on Feb. 24, 2021.

(30) Foreign Application Priority Data

Mar. 12, 2020 (JP) .................................. 2020043497

(51) Int. Cl.
*A61M 1/18* (2006.01)
*A61M 1/16* (2006.01)
(Continued)

(52) U.S. Cl.
CPC ........ *A61M 1/1698* (2013.01); *A61M 1/1621* (2014.02); *B01D 71/262* (2022.08); *B01D 71/60* (2013.01); *A61M 2207/00* (2013.01)

(58) Field of Classification Search
CPC .............. A61M 1/1698; A61M 1/1621; A61M 2207/00; B01D 2321/281; B01D 71/262;
(Continued)

(56) References Cited

U.S. PATENT DOCUMENTS

2012/0048805 A1* 3/2012 McCutcheon ..... B01D 69/1216
427/244
2013/0240445 A1* 9/2013 Vizvardi ............ B01D 67/0088
210/500.33

(Continued)

FOREIGN PATENT DOCUMENTS

CN 104150787 A 11/2014
CN 107174976 A 9/2017
(Continued)

OTHER PUBLICATIONS

International Search Report, PCT/JP2021/006775, Apr. 15, 2021.
International Preliminary Opinion, PCT/JP2021/006775, Apr. 27, 2021.

*Primary Examiner* — Frank M Lawrence, Jr.
(74) *Attorney, Agent, or Firm* — MacMillan, Sobanski & Todd, LLC

(57) ABSTRACT

An oxygenator has a plurality of porous hollow fiber membranes comprising polypropylene for gas exchange, wherein each hollow fiber membrane has an inner surface that forms a lumen and an outer surface. The oxygenator is manufactured using a method which involves preparing a coating solution containing at least one compound selected from the group consisting of dopamine, salt of dopamine, and oligomer of dopamine; and bringing the inner surface or the outer surface of the hollow fiber membranes into contact with the coating solution for less than ten hours while blowing oxygen gas in the coating solution to form a dopamine polymer layer containing a polymer of the compound on the inner surface or the outer surface.

20 Claims, 10 Drawing Sheets

(51) Int. Cl.
*B01D 71/26* (2006.01)
*B01D 71/60* (2006.01)

(58) Field of Classification Search
CPC ............... B01D 71/60; B01D 67/0088; B01D 2053/224
USPC ................... 95/43, 45, 54; 96/4, 8, 10–12
See application file for complete search history.

(56) References Cited

U.S. PATENT DOCUMENTS

| | | | |
|---|---|---|---|
| 2018/0126316 A1 | 5/2018 | Seo et al. | |
| 2018/0147533 A1 | 5/2018 | Seo et al. | |
| 2021/0121831 A1* | 4/2021 | Aljundi | B01D 69/148 |
| 2024/0325988 A1* | 10/2024 | Baig | B01D 67/00793 |
| 2025/0050284 A1* | 2/2025 | Swartjes | A61M 1/34 |

FOREIGN PATENT DOCUMENTS

| | | | |
|---|---|---|---|
| CN | 108722200 A | 11/2018 |
| CN | 108722207 A | 11/2018 |
| JP | 2002035116 A | 2/2002 |

* cited by examiner

METHOD FOR MANUFACTURING OXYGENATOR

CROSS REFERENCE TO RELATED APPLICATIONS

This application is a continuation of PCT Application No. PCT/JP2021/006775, filed Feb. 24, 2021, based on and claiming priority to Japanese Application No. JP2020-043497, filed Mar. 12, 2020, both of which are incorporated herein by reference in their entirety.

BACKGROUND OF THE INVENTION

The present invention relates to a method for manufacturing an oxygenator.

An oxygenator including porous hollow fiber membranes may have a decrease in gas exchange performance with long-term use. Wet lung and plasma leakage are main factors of the decrease in performance. It is possible to recover the gas exchange performance of a wet lung by blowing air at high pressure to remove dew condensation from hollow fiber membranes. In contrast, plasma leakage causes an irreversible decrease in performance of an oxygenator. Finding a solution to the problem caused by plasma leakage is a requirement for long-term use of oxygenators, and many studies have been made so far. In order to improve anti-plasma leakage properties, the following approaches have been employed in the studies: an approach for closing micropores in hollow fiber membranes, and an approach for making micropores in hollow fiber membranes ultrafine.

For example, according to JP 2002-035116A, a silicone coating applied to an outer surface of polypropylene porous hollow fiber membranes reduces the chance of plasma leakage and enables long-term use.

However, in the technique disclosed in JP 2002-035116A, the silicone coating is applied by moving a continuous line of the hollow fiber membranes at a rate of 0.5 to 50 m/min in a silicone monomer gas during plasma discharge in a high vacuum and by polymerizing silicone monomers on the outer surface of the hollow fiber membranes. For this reason, the coating in this technique requires intricate equipment and long periods of time.

SUMMARY OF THE INVENTION

An object of the invention is to provide a method for manufacturing an oxygenator by a simpler technique.

The inventors have found that the object is achieved by bringing a coating solution containing dopamine (or a salt or oligomer thereof) into contact with polypropylene porous hollow fiber membranes while blowing oxygen gas, thereby completing the invention.

That is, the object is achieved by a method for manufacturing an oxygenator having a plurality of porous hollow fiber membranes for gas exchange, at least part of which includes polypropylene and each of which has an inner surface that forms a lumen and an outer surface, in which the method involves preparing a coating solution containing at least one compound selected from the group consisting of dopamine, salt of dopamine, and oligomer of dopamine; and bringing the inner surface or the outer surface of the hollow fiber membranes into contact with the coating solution for less than ten hours while blowing oxygen gas in the coating solution to form a polymer layer containing a polymer of the compound on the inner surface or the outer surface.

DETAILED DESCRIPTION OF PREFERRED EMBODIMENTS

Figure 1:
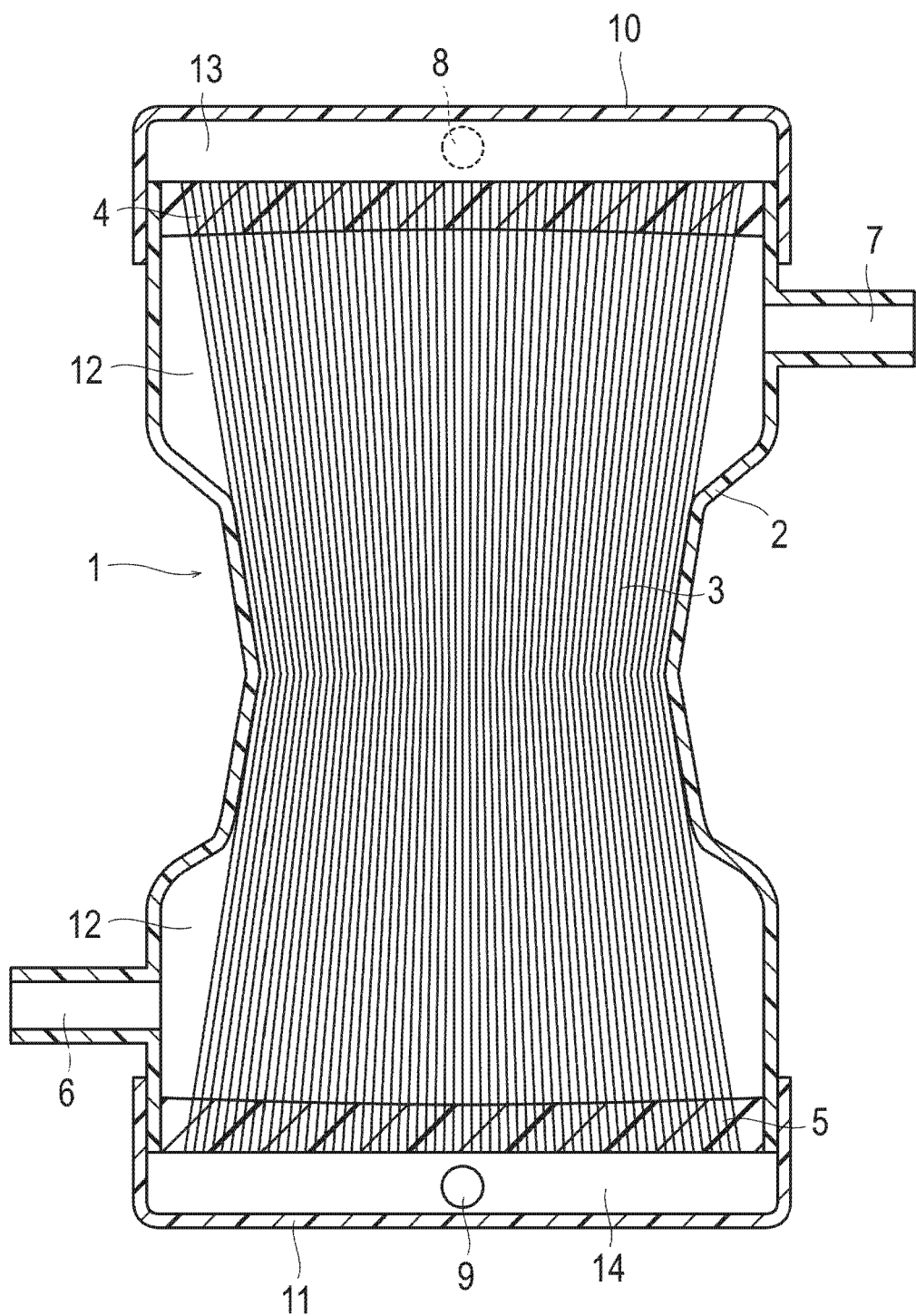
FIG. 1 is a cross-sectional view of a hollow fiber membrane-based oxygenator of external perfusion type according to an embodiment of the invention.

The invention relates to a method for manufacturing an oxygenator having a plurality of porous hollow fiber membranes for gas exchange, at least part of which includes polypropylene and each of which has an inner surface that forms a lumen and an outer surface, in which the method involves: preparing a coating solution containing at least one compound selected from the group consisting of dopamine, salt of dopamine, and oligomer of dopamine; and bringing the inner surface or the outer surface of the hollow fiber membranes into contact with the coating solution for less than ten hours while blowing oxygen gas in the coating solution to form a polymer layer containing a polymer of the compound on the inner surface or the outer surface. According to the invention, it is possible to provide an oxygenator by a simpler technique. Herein, "at least one compound selected from the group consisting of dopamine, salt of dopamine, and oligomer of dopamine" is also referred to as "polymer layer forming compound".

The method for manufacturing an oxygenator according to the invention offers an oxygenator by a technique simpler than one employed in the manufacturing method disclosed in JP 2002-035116A. The following chemical process is inferred to achieve the effects of the invention. Note that the following chemical process is based on inference, and the invention is not limited to the following inferred explanation.

In the method of the invention, a coating solution containing a polymer layer forming compound is brought into contact with a surface of hollow fiber membranes for a predetermined time while oxygen gas is blown to the coating solution, and the polymer layer forming compound is polymerized on the surface of the hollow fiber membranes to form a polymer layer on the surface of the hollow fiber membranes. For example, dopamine typically produces 5,6- dihydroxyindole by oxidation. Polymerization of this compound forms and deposits a dopamine polymer (polydopamine) on a substrate, thereby forming a dopamine polymer layer. Accordingly, the method of the invention enables manufacturing of an oxygenator by an operation as simple as bringing the coating solution containing the polymer layer forming compound such as dopamine (or a salt or oligomer thereof) into contact with the surface of the hollow fiber membranes. In addition, as in the invention, bringing the coating solution containing the polymer layer forming compound such as dopamine (or a salt or oligomer thereof) into contact with the surface of the hollow fiber membranes while blowing oxygen gas proceeds reactions (for example, oxidation and polymerization of dopamine) of the polymer layer forming compound more quickly and efficiently. Oxygen gas easily passes in the thickness direction of the hollow fiber membranes through lumina and pores of the hollow fiber membranes with small diameters. Accordingly, in the method of the invention, the reactions (for example, oxidation and polymerization of dopamine) of the polymer layer forming compound rapidly proceed on the surface of the hollow fiber membranes, which enables formation of a polymer layer having a predetermined thickness by a simple operation and in less time. If the contact between the coating solution and the hollow fiber membranes lasts for an excessive time (e.g., ten hours or more), the reactions of the polymer layer forming compound proceed excessively and the layer becomes thick, which decreases gas exchange performance (gas transmission rate). Therefore, an oxygenator manufactured by the method of the invention has excellent gas exchange performance (gas permeability).

Furthermore, according to the method of the invention, it is possible to bring the coating solution containing a compound such as dopamine (or a salt thereof) into contact with the surface of the hollow fiber membranes while blowing oxygen gas after assembling an oxygenator (or a hollow fiber membrane bundle). Therefore, the method of the invention is also preferable from perspectives of productivity and mass production.

In addition, a reactant of the polymer layer forming compound according to the invention (particularly, a dopamine polymer (polydopamine)) has high reactivity with an organic substance, and the polymer layer according to the invention (dopamine polymer layer; the same applies hereinafter) is highly reactive. For this reason, the polymer layer has high adhesion to polypropylene hollow fiber membranes. Furthermore, when an antithrombotic drug layer is formed on the polymer layer, the reactant of the polymer layer forming compound in the polymer layer (particularly, polydopamine) also exhibits high reactivity with an antithrombotic drug (for example, polymethoxyethyl (meth) acrylate) of the antithrombotic drug layer. For this reason, the polymer layer exerts high reactivity with the antithrombotic drug and has high adhesion with the antithrombotic drug layer. That is, it is possible to integrate the antithrombotic drug layer firmly with the hollow fiber membranes via the polymer layer. For these reasons, an oxygenator manufactured by the method of the invention has excellent effects of the antithrombotic drug (such as antithrombogenicity) and excellent anti-plasma leakage properties and is capable of maintaining the antithrombogenicity and the anti-plasma leakage properties even after a month of use or more (that is, the oxygenator has excellent antithrombogenicity, anti-plasma leakage properties, and maintainability of the anti-thrombogenicity and the anti-plasma leakage properties).

Accordingly, an oxygenator manufactured by the method of the invention is preferably usable not only as an oxygenator for normal surgery but also as a pulmonary circulation and support for a patient with a serious disease.

Hereinafter, preferred embodiments of the invention will be described. Note that the invention is not limited to the following embodiments. Furthermore, dimensional ratios of the drawings are exaggerated for illustration purpose and may differ from actual ratios.

Herein, "X to Y" represents a range including X and Y, indicating "X or more and Y or less". Unless otherwise specified, operations and measurements of physical properties and the like are performed at room temperature (20 to 25° C.) and at relative humidity of 40 to 50% RH. The expression "A and/or B" indicates at least one of A and B and includes "A", "B", and "combination of A and B".

Hereinafter, a method for manufacturing an oxygenator according to the invention will be described in detail. For convenience, an oxygenator obtained by the manufacturing method of the invention will be described first, and then, the manufacturing method of the invention will be described.

Oxygenator

An oxygenator according to an embodiment of the invention has a plurality of porous hollow fiber membranes for gas exchange, at least part of which includes polypropylene and each of which has an inner surface that forms a lumen and an outer surface. A polymer layer and an antithrombotic drug layer formed by the method of the invention are disposed on at least one of the inner surface and the outer surface in this order (that is, the hollow fiber membranes, the polymer layer, and the antithrombotic drug layer are disposed in this order). The oxygenator according to the invention exhibits high anti-plasma leakage properties and effects of an antithrombotic drug (such as antithrombogenicity) and is capable of maintaining the anti-plasma leakage properties and the antithrombogenicity even after a month of use or more (that is, the oxygenator is excellent in anti-plasma leakage properties, antithrombogenicity, maintainability of the anti-plasma leakage properties and the antithrombogenicity). For these reasons, it is particularly preferable to use the oxygenator according to the invention as an extracorporeal circulation machine such as extra corporeal membrane oxygenation (ECMO) and percutaneous cardio pulmonary support (PCPS) in order to support respiration and circulation of patients with circulatory failure such as pneumonia, severe respiratory failure, acute myocardial infarction, and acute myocarditis. Hereinafter, the polymer layer formed by the method of the invention is simply referred to as "polymer layer according to the invention" or "polymer layer".

Details of the oxygenator according to the invention will now be described with reference to the drawings.

Figure 2:
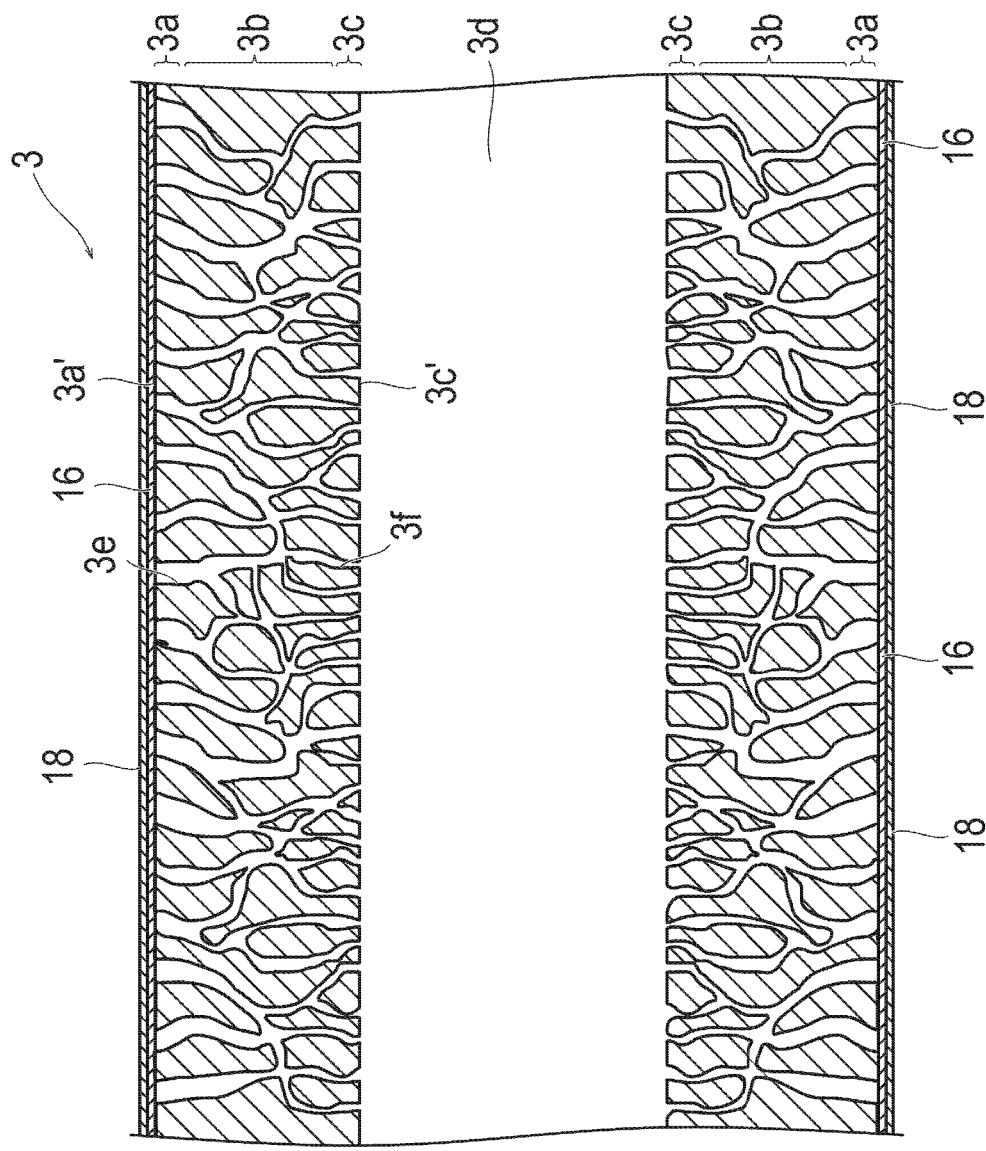
FIG. 2 is an enlarged cross-sectional view of a porous hollow fiber membrane for gas exchange used in the hollow fiber membrane-based oxygenator of external perfusion type according to the embodiment of the invention.

FIG. 1 is a cross-sectional view of a hollow fiber membrane-based oxygenator of external perfusion type according to an embodiment of the invention. FIG. 2 is an enlarged cross-sectional view of a porous hollow fiber membrane for gas exchange used in the hollow fiber membrane-based oxygenator of external perfusion type according to the embodiment of the invention.

In the embodiment illustrated in FIG. 1, a hollow fiber membrane-based oxygenator of external perfusion type 1 includes a large number of porous hollow fiber membranes 3 for gas exchange placed in a housing 2. As illustrated in FIG. 2, the hollow fiber membranes 3 each include a passageway (lumen) 3d having a gas chamber at the center. Herein, in a case where an oxygen-containing gas flows into the lumina 3d, blood flows outside (through an outer surface 3a' of) the hollow fiber membranes 3 (hollow fiber membrane-based oxygenator of external perfusion type). Similarly, in a case where blood flows into the lumina 3*d*, the oxygen-containing gas flows outside (through the outer surface 3*a'* of) the hollow fiber membranes 3 (hollow fiber membrane-based oxygenator of internal perfusion type). The invention may employ any of the above embodiments. However, it is preferable that the oxygen-containing gas flows into the lumina 3*d*, and blood flows outside (through the outer surface 3*a'* of) the hollow fiber membranes 3. In addition, the hollow fiber membranes 3 have openings 3*e* and 3*f* through which an outer surface 3*a'* and an inner surface 3*c'* of the hollow fiber membranes 3 communicate with each other. A polymer layer 16 and an antithrombotic drug layer 18 are formed in this order on at least one of the inner surface 3*c'* and the outer surface 3*a'* of the hollow fiber membranes 3 (that is, the hollow fiber membranes, the polymer layer, and the antithrombotic drug layer are formed in this order). Herein, the polymer layer 16 and the antithrombotic drug layer 18 are preferably disposed at least on the side where blood flows. In other words, the polymer layer 16 and the antithrombotic drug layer 18 are preferably formed at least on the outer surface 3*a'* of the hollow fiber membranes 3, and are more preferably formed on the outer surface 3*a'* of the hollow fiber membranes 3 in consideration of the effect of further improving gas permeability. In FIG. 2, the polymer layer 16 is disposed on the outer surface 3*a'* of the hollow fiber membranes 3, but the polymer layer 16 may be disposed on the inner surface 3*c'* of the hollow fiber membranes 3. In FIG. 2, the polymer layer 16 is disposed immediately above the hollow fiber membranes 3, but the polymer layer 16 may be disposed on the hollow fiber membranes 3 via another layer. Preferably, the polymer layer 16 is disposed on the outer surface 3*a'* of the hollow fiber membranes 3, and more preferably the polymer layer 16 is disposed directly on the outer surface 3*a'* of the hollow fiber membranes 3.

The polymer layer 16 and the antithrombotic drug layer 18 according to the invention may be formed on at least part of the inner surface 3*c'* and/or the outer surface 3*a'* of the hollow fiber membranes 3. However, from a perspective of maintaining gas exchange performance in long-term use (or from perspectives of improving anti-plasma leakage properties and suppressing wet lung), the polymer layer 16 and the antithrombotic drug layer 18 are preferably formed on the entire inner surface 3*c'* and/or outer surface 3*a'*, and more preferably formed on the entire outer surface 3*a'*. As illustrated in FIG. 2, the polymer layer 16 according to the invention is preferably formed as a homogeneous film that closes pores of the hollow fiber membranes 3. With such an embodiment, it is possible to suppress the leakage of plasma through the pores of the hollow fiber membranes and to further improve the anti-plasma leakage properties of the oxygenator. Accordingly, that the oxygenator having this structure can be used for a longer period of time. Even in this embodiment, the polymer layer 16 and the antithrombotic drug layer 18 have high gas permeability, and thus, have sufficient gas exchange performance.

Furthermore, the antithrombotic drug layer 18 containing an antithrombotic drug may be formed on at least part of the polymer layer 16 but is preferably formed on the entire polymer layer 16 from perspectives of antithrombogenicity (or from perspectives of suppressing and preventing adhesion/attachment of platelets and suppressing and preventing activation of platelets), maintainability of the antithrombogenicity (durability), and anti-plasma leakage properties. In the embodiment illustrated in FIG. 2, the polymer layer 16 and the antithrombotic drug layer 18 may be in the middle layer 3*b* of the hollow fiber membranes 3 (or the middle layer 3*b* and the inner layer 3*c* according to circumstances). However, it is preferable that the polymer layer 16 and the antithrombotic drug layer 18 are substantially not in the middle layer 3*b* of the hollow fiber membranes 3 (or the middle layer 3*b* and the inner layer 3*c* according to circumstances). When the middle layer 3*b* or the inner layer 3*c* of the hollow fiber membranes 3 is substantially free from the antithrombotic drug, hydrophobic properties of a base material contained in the middle layer 3*b* or the inner layer 3*c* are maintained, which prevents leakage of plasma components effectively. Herein, the expression "the antithrombotic drug layer 18 containing an antithrombotic drug is substantially not in the middle layer 3*b* of the hollow fiber membranes 3 (or the middle layer 3*b* and the inner layer 3*c* according to circumstances)" indicates that penetration of the antithrombotic drug is not observed around the inner surface 3*c'* of the hollow fiber membranes 3 (a surface on the side where the oxygen-containing gas flows). As will be described in a preferred embodiment of the method for manufacturing an oxygenator, when forming a polymer layer, the polymer layer forming compound is substantially not in the middle layer 3*b* or the inner layer 3*c* of the hollow fiber membranes 3. Similarly, as will be described in a preferred embodiment of the method for manufacturing an oxygenator, a coating is formed by applying a colloid solution containing an antithrombotic polymer compound, whereby the antithrombotic polymer compound is substantially not in the middle layer 3*b* or the inner layer 3*c* of the hollow fiber membranes 3.

In other words, according to a particularly preferred embodiment of the invention, the oxygen-containing gas flows into the lumina of the hollow fiber membranes, blood flows outside (through the outer surface of) the hollow fiber membranes, and the polymer layer and the antithrombotic drug layer are formed in this order on the entire outer surface (blood contact portion) of the hollow fiber membranes (oxygenator of external perfusion type).

The polymer layer 16 may contain other components in addition to the dopamine polymer (polydopamine). Examples of the other components include, but are not particularly limited to, polyolefins, aliphatic hydrocarbons, inorganic fine particles, and hydrophilic polymers. Preferably, the polymer layer 16 substantially consists of a dopamine polymer (polydopamine), and more preferably, the polymer layer 16 consists of a dopamine polymer (polydopamine). Herein, the phrase "the polymer layer 16 substantially consists of a dopamine polymer (polydopamine)" indicates that the polymer layer 16 contains a component other than the dopamine polymer (polydopamine) (for example, dopamine or a salt thereof) at a ratio of less than 5% by mass (in solid content).

Similarly, the antithrombotic drug layer 18 may contain other components in addition to the antithrombotic polymer compound (for example, an antithrombotic drug represented by Formula (1) and heparin). Examples of the other components include, but are not particularly limited to, cross-linkers, thickeners, preservatives, pH adjusters, and amphipathic substances. Preferably, the antithrombotic drug layer 18 substantially consists of an antithrombotic drug, and more preferably, the antithrombotic drug layer 18 consists of an antithrombotic drug. Herein, the expression "the antithrombotic drug layer 18 substantially consists of an antithrombotic drug" indicates that the antithrombotic drug layer 18 contains components other than the antithrombotic drug at a ratio of less than 5% by mass (in solid content).

The hollow fiber membrane-based oxygenator 1 according to this embodiment is provided with the housing 2 including a blood inlet 6 and a blood outlet 7, a hollow fiber membrane bundle including a large number of porous hollow fiber membranes 3 for gas exchange placed in the housing 2, a pair of partitions 4 and 5 configured to hold both ends of the hollow fiber membrane bundle to the housing 2 in a liquid-tight manner, a blood chamber 12 formed between inner surfaces of the partitions 4, 5 and the housing 2 and the outer surface of the hollow fiber membranes 3, a gas chamber formed inside the hollow fiber membranes 3, and a gas inlet 8 and a gas outlet 9 that communicate with the gas chamber.

Specifically, the hollow fiber membrane-based oxygenator 1 according to this embodiment includes the housing 2 having a tubular shape, an aggregate of the hollow fiber membranes 3 for gas exchange housed in the tubular housing 2, and the partitions 4 and 5 that hold both ends of the hollow fiber membranes 3 placed in the housing 2 in a liquid-tight manner. The interior of the tubular housing 2 is partitioned into the blood chamber 12 as a first fluid chamber and the gas chamber as a second fluid chamber. The tubular housing 2 is provided with the blood inlet 6 and the blood outlet 7 that communicate with the blood chamber 12.

A gas inlet header 10 having a cap shape is attached to the top of the partition 4 or an end of the tubular housing 2. The gas inlet header 10 includes the gas inlet 8 or a second fluid inlet that communicates with the gas chamber or an internal space of the hollow fiber membranes 3. With such a configuration, an outer surface of the partition 4 and an inner surface of the gas inlet header 10 form a gas inlet chamber 13. This gas inlet chamber 13 communicates with the gas chamber formed by the internal space of the hollow fiber membranes 3.

Similarly, a gas outlet header 11 having a cap shape is attached to the bottom of the partition 5. The gas outlet header 11 includes the gas outlet 9 or a second fluid outlet that communicates with the internal space of the hollow fiber membranes 3. With such a configuration, an outer surface of the partition 5 and an inner surface of the gas outlet header 11 form a gas outlet chamber 14.

The hollow fiber membranes 3 are porous membranes at least part of which includes polypropylene. Herein, the hollow fiber membranes 3 may partially include polypropylene and the other part may include materials (other materials) other than polypropylene or may partially or entirely include polypropylene and other materials. Preferably, the hollow fiber membranes 3 consist of polypropylene. Examples of the other materials include, but are not particularly limited to, those similar to hollow fiber membranes employed in a known oxygenator. Forming the hollow fiber membranes 3 (particularly, the inner surface 3c' of the hollow fiber membranes 3) with a hydrophobic polymer material suppresses leakage of plasma components. An example of a material used for porous membranes includes one similar to a hydrophobic polymer material included in hollow fiber membranes of a known oxygenator. Specific examples of the material include polyolefin resins such as polyethylene and polymethylpentene and polymer materials such as polysulfone, polyacrylonitrile, polytetrafluoroethylene, and cellulose acetate. Among these examples, polyolefin resin is preferable, and polymethylpentene is more preferable. In a case where the hollow fiber membranes 3 include polypropylene and other materials as described above, the polypropylene content is typically more than 70 mass % (in solid content), preferably 80 mass % (in solid content) or more, and more preferably 90 mass % (in solid content) or more (upper limit: less than 100 mass %) with respect to the total amount of materials included in the hollow fiber membranes.

The hollow fiber membranes 3 preferably have an inside diameter of 50 to 300 μm and more preferably 80 to 200 μm but are not particularly limited thereto. The hollow fiber membranes 3 preferably have an outside diameter of 100 to 400 μm and more preferably 130 to 200 μm but are not particularly limited thereto. The hollow fiber membranes 3 preferably have a thickness (membrane thickness) of 20 μm or more and less than 50 μm, more preferably 25 μm or more and less than 50 μm, still more preferably 25 to 45 μm, still more preferably 25 to 40 μm, still more preferably 25 to 35 μm, and particularly preferably 25 to 30 μm. Herein, the "thickness (membrane thickness)" of the hollow fiber membranes 3 indicates a thickness between the inner surface 3c' and the outer surface 3a' of the hollow fiber membranes 3, which is calculated by the Formula: [(outside diameter of hollow fiber membrane)−(inside diameter of hollow fiber membrane)]/2. With a minimum thickness falling within the above ranges, it is possible to sufficiently ensure the strength of the hollow fiber membranes 3. Furthermore, it is possible to satisfactorily save the trouble and cost during manufacturing, which is also preferable from a perspective of mass production. The hollow fiber membranes 3 preferably have a porosity of 5 to 90 vol. %, more preferably 10 to 80 vol. %, and particularly preferably 30 to 60 vol. %. The hollow fiber membranes 3 preferably have a pore size of 0.01 to 5 μm and more preferably 0.05 to 1 μm A method for producing hollow fiber membranes is not particularly limited and may be similar to a known method for producing hollow fiber membranes or a modification of the known method. For example, hollow fiber membranes are preferably prepared by forming micropores in a wall by stretching or solid-liquid phase separation.

Herein, the "pore size" of the hollow fiber membranes 3 refers to an average diameter of openings on the side covered with the antithrombotic drug (outer surface). Pore sizes of hollow fiber membranes are measured by the following method.

First, a scanning electron microscope (SEM) is used to capture an image of one side (outer surface) of hollow fiber membranes covered with an antithrombotic drug. Next, the obtained SEM image is subject to image processing, and pores (openings) are reassigned a pixel value for white and the other portions reassigned for black based on a threshold, and the number of pixels of the white portions is measured. The threshold for performing binarization may be set to an intermediate value between the whitest (brightest) portion and the blackest (darkest) portion before binarization.

The next step is to count the number of pixels of the pores (openings) displayed with white. Based on the number of pixels of the pores obtained in this manner and the resolution (μm/pixel) of the SEM image, pore areas are calculated. From the obtained pore areas, diameters of the pores are calculated assuming that the pores are circular, and a statistically significant number of pores, for example, 500 pores are randomly extracted. An arithmetic average diameter of the pores is referred to as the "pore size" of the hollow fiber membranes.

A material included in the tubular housing 2 may also be similar to one used for a housing of a known oxygenator. Specific examples of the material include hydrophobic synthetic resins such as polycarbonate, acryl-styrene copolymers, and acryl-butylene-styrene copolymers. The housing 2 is not particularly limited in shape and has, for example, a cylindrical shape and preferably has a transparent body. A transparent body makes it possible to check the inside of the housing 2 easily.

The quantity of the hollow fiber membranes 3 housed in this embodiment is not particularly limited and may be similar to that in a known oxygenator. For example, about 5,000 to 100,000 porous hollow fiber membranes 3 are axially placed in the housing 2 in parallel. Furthermore, the hollow fiber membranes 3 are fixed to both ends of the housing 2 in a liquid-tight state by the partitions 4 and 5 with both ends of the hollow fiber membranes 3 being opened. The partitions 4 and 5 are formed with a potting agent such as polyurethane and silicone rubber. A portion within the housing 2 sandwiched between the partitions 4 and 5 is partitioned into the gas chamber inside the hollow fiber membranes 3 and the blood chamber 12 outside the hollow fiber membranes 3.

In this embodiment, the gas inlet header 10 including the gas inlet 8 and the gas outlet header 11 including the gas outlet 9 are attached to the housing 2 in a liquid-tight manner. These headers 10 and 11 may be formed with any material, for example, a hydrophobic synthetic resin used for the housing 2. These headers 10 and 11 may be attached by any method. For example, the headers 10 and 11 are attached to the housing 2 by fusion using ultrasonic waves, high frequency, or induction heating, by adhesion using an adhesive, or by mechanical fitting. Alternatively, a fastening ring (not illustrated) may be used. The blood contact portion (an inner surface of the housing 2 or the outer surface 3a' of the hollow fiber membranes 3) of the hollow fiber membrane-based oxygenator 1 preferably consists of a hydrophobic material.

In this embodiment, the antithrombotic drug layer 18 is selectively formed on the outer surface 3a' of the hollow fiber membranes 3 (of external perfusion type). With such a configuration, blood (specifically, plasma components) hardly permeates or does not permeate the pores of the hollow fiber membranes 3. Accordingly, it is possible to effectively suppress and prevent leakage of blood (specifically, plasma components) from the hollow fiber membranes 3. Specifically, in a case where the antithrombotic drug is substantially not in the middle layer 3b and the inner layer 3c of the hollow fiber membranes 3, it is possible to suppress and prevent leakage of high blood (specifically, plasma components) more effectively because materials of the middle layer 3b and the inner layer 3c of the hollow fiber membranes 3 maintain a hydrophobic state. Accordingly, an oxygenator obtained by the method of the invention maintains high gas exchange performance over a long period of time.

The antithrombotic drug-containing covering (antithrombotic drug layer) according to this embodiment is formed on the polymer layer 16 of the inner surface 3c' and/or the outer surface 3a' of the hollow fiber membranes 3 of the oxygenator 1 but may be formed on other components (for example, the entire blood contact portion) in addition to the inner surface 3c' and/or the outer surface 3a'. With such a configuration, the oxygenator 1 is capable of suppressing and preventing adhesion/attachment and activation of platelets more effectively in the entire blood contact portion. Furthermore, such a configuration reduces a contact angle of the blood contact surface and facilitates priming. In this case, the antithrombotic drug-containing covering according to the invention is preferably formed on other components to which blood comes into contact, but note that the hollow fiber membranes 3 other than the blood contact portion or other portions of the hollow fiber membranes 3 (for example, portions buried in the partitions 4 and 5) are not necessarily covered with the antithrombotic drug. Since these portions do not come into contact with blood, it matters little if the portions are not covered with the antithrombotic drug.

Figure 3:
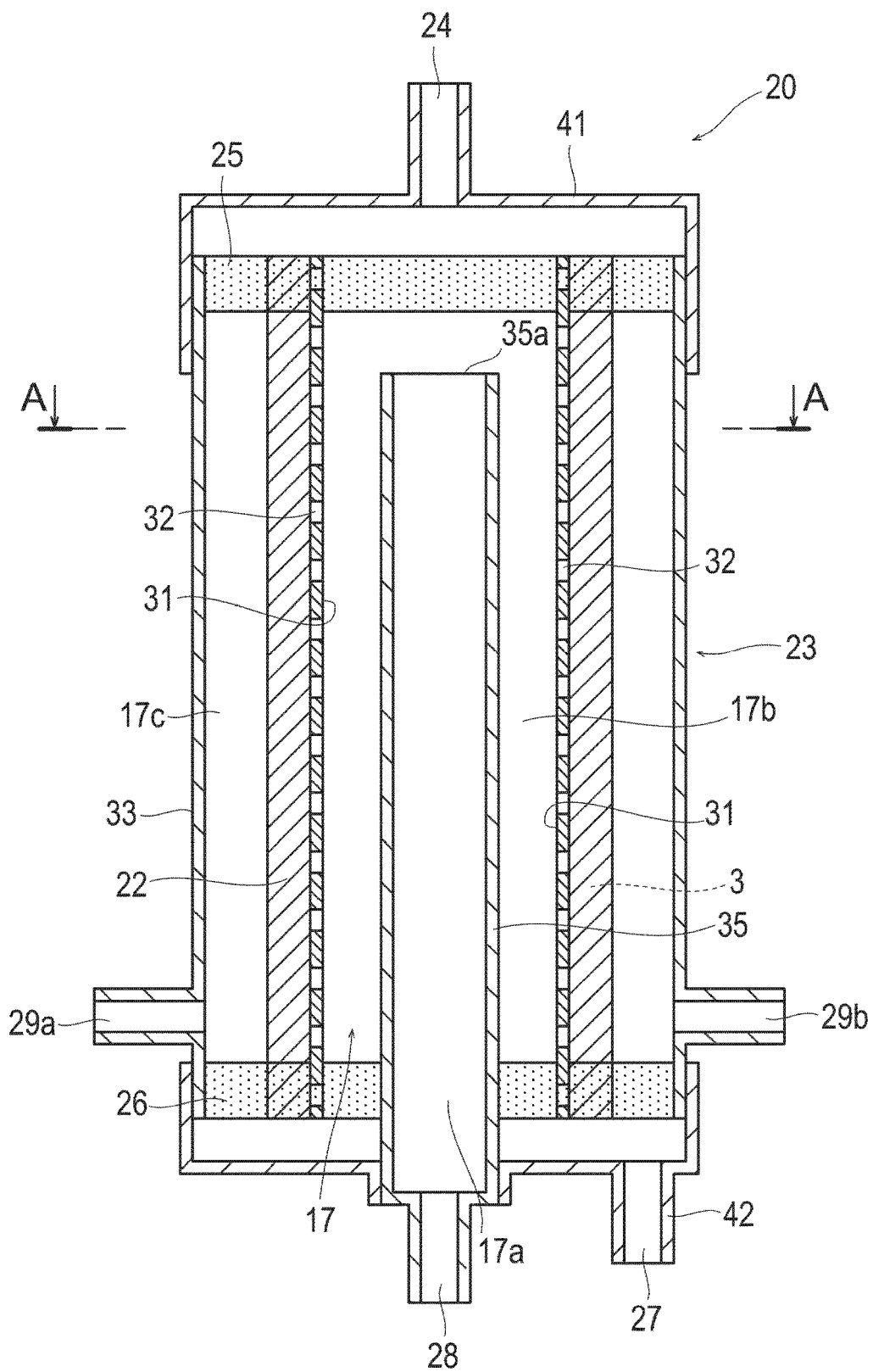
FIG. 3 is a cross-sectional view of a hollow fiber membrane-based oxygenator of external perfusion type according to another embodiment of the invention.
Figure 4:
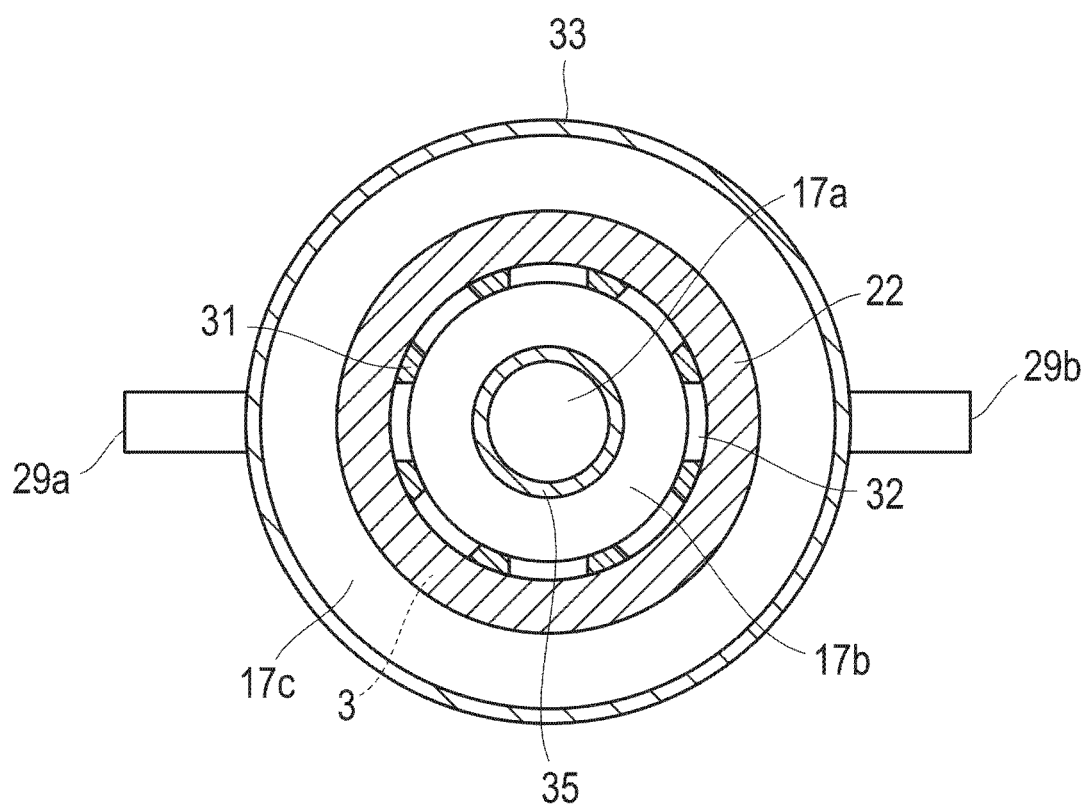
FIG. 4 is a cross-sectional view taken along line A-A of FIG. 3.

An oxygenator obtained by the method according to the invention may also be of the type illustrated in FIG. 3. FIG. 3 is a cross-sectional view illustrating another embodiment of an oxygenator obtained by the method according to the invention. FIG. 4 is a cross-sectional view taken along line A-A of FIG. 3.

In FIG. 3, an oxygenator (hollow fiber membrane-based oxygenator of external perfusion type) 20 includes an inner tube 31 having a side surface provided with openings 32 for blood circulation, a tubular hollow fiber membrane bundle 22 including a large number of porous hollow fiber membranes 3 for gas exchange and wound around an outer surface of the inner tube 31, a housing 23 that stores the tubular hollow fiber membrane bundle 22 together with the inner tube 31, partitions 25 and 26 that fix both ends of the tubular hollow fiber membrane bundle 22 to the housing 23 while both ends of the hollow fiber membranes 3 are opened, a blood inlet 28 and blood outlets 29a and 29b that communicate with a blood chamber 17 formed in the housing 23, and a gas inlet 24 and a gas outlet 27 that communicate with the inside of the hollow fiber membranes 3.

In the oxygenator 20 according to this embodiment, as illustrated in FIGS. 3 and 4, the housing 23 includes an outer tube 33 for housing the inner tube 31, and the tubular hollow fiber membrane bundle 22 is placed between the inner tube 31 and the outer tube 33. Furthermore, the housing 23 is provided with one of the blood inlet 28 and blood outlets 29a and 29b which communicates with the inside of the inner tube 31 and the other of the blood inlet 28 and blood outlets 29a and 29b which communicates with the inside of the outer tube 33.

Specifically, the oxygenator 20 of this embodiment includes the housing 23 provided with an inner cannula 35 that is housed in the outer tube 33 and the inner tube 31 and has a distal end opened inside the inner tube 31. One end (the bottom) of the inner cannula 35 is provided with the blood inlet 28. The side surface of the outer tube 33 is provided with the two blood outlets 29a and 29b that stretch outward. The number of blood outlets may be one or more.

The tubular hollow fiber membrane bundle 22 is wound around the outer surface of the inner tube 31. In other words, the inner tube 31 is a core of the tubular hollow fiber membrane bundle 22. The inner cannula 35 housed in the inner tube 31 has the distal end opened near the first partition 25. Furthermore, the bottom of the inner cannula 35 protruded from the inner tube 31 is provided with the blood inlet 28.

The inner cannula 35, the inner tube 31 having the outer surface wound by the hollow fiber membrane bundle 22, and the outer tube 33 are substantially concentric. Due to the first partition 25, one end (upper end) of the inner tube 31 having the outer surface wound by the hollow fiber membrane bundle 22 and one end (upper end) of the outer tube 33 maintain concentric positions and are in a liquid-tight state so that the inside of the inner tube 31 and a space between the outer tube 33 and the outer surface of the hollow fiber membranes 3 do not communicate with the outside.

Furthermore, portions slightly upper than the blood inlet 28 of the inner cannula 35, that is, the other end (lower end) of the inner tube 31 having the outer surface wound by the hollow fiber membrane bundle 22 and the other end (lower end) of the outer tube 33, maintain concentric positions by the second partition 26 and are in a liquid-tight state so that a space between the inner cannula 35 and the inner tube 31 and a space between the outer tube 33 and the outer surface of the hollow fiber membranes 3 do not communicate with the outside. The partitions 25 and 26 are formed with a potting agent such as polyurethane or silicone rubber.

Accordingly, the oxygenator 20 of this embodiment includes a blood inlet 17a formed by the inside of the inner cannula 35, a first blood chamber 17b that is formed between the inner cannula 35 and the inner tube 31 and is substantially formed into a tubular space, and a second blood chamber 17c that is formed between the hollow fiber membrane bundle 22 and the outer tube 33 and is substantially formed into a tubular space. The blood inlet 17a, first blood chamber 17b, and second blood chamber 17c form the blood chamber 17.

The blood flowing in from the blood inlet 28 flows into the blood inlet 17a, rises within the inner cannula 35 (blood inlet 17a), flows out from an upper end 35a (opening end) of the inner cannula 35, flows into the first blood chamber 17b, passes through the openings 32 formed in the inner tube 31, and comes into contact with the hollow fiber membranes 3. After gas exchange, the blood flows into the second blood chamber 17c and flows out from the blood outlets 29a and 29b.

A gas inlet member 41 including the gas inlet 24 is fixed to one end of the outer tube 33. Similarly, a gas outlet member 42 including the gas outlet 27 is fixed to the other end of the outer tube 33. The blood inlet 28 of the inner cannula 35 penetrates the gas outlet member 42 and protrudes to the outside.

The outer tube 33 is not particularly limited in shape and may be shaped into, for example, a cylinder or polygonal tube, or a tube having an elliptical cross-section. A cylinder is preferable. The outer tube 33 is not particularly limited in inside diameter and may have a similar inside diameter to that of an outer tube used for a known oxygenator. However, a preferable inside diameter is about 32 to 164 mm. The outer tube 33 is not particularly limited in effective length (a range within the entire length which is not buried in the partitions 25 and 26) and may have a similar effective length to that of an outer tube used for a known oxygenator. However, a preferable effective length is about 10 to 730 mm.

The inner tube 31 is not particularly limited in shape and may be shaped into, for example, a cylinder, polygonal tube, or a tube having an elliptical cross-section. A cylinder is preferable. The inner tube 31 is not particularly limited in outside diameter and may have a similar outside diameter to that of an inner tube used for a known oxygenator. However, a preferable outside diameter is about 20 to 100 mm. The inner tube 31 is not particularly limited in effective length (a range within the entire length which is not buried in the partitions 25 and 26) and may have a similar effective length to that of an inner tube used for a known oxygenator. However, a preferable effective length is about 10 to 730 mm.

Figure 5:
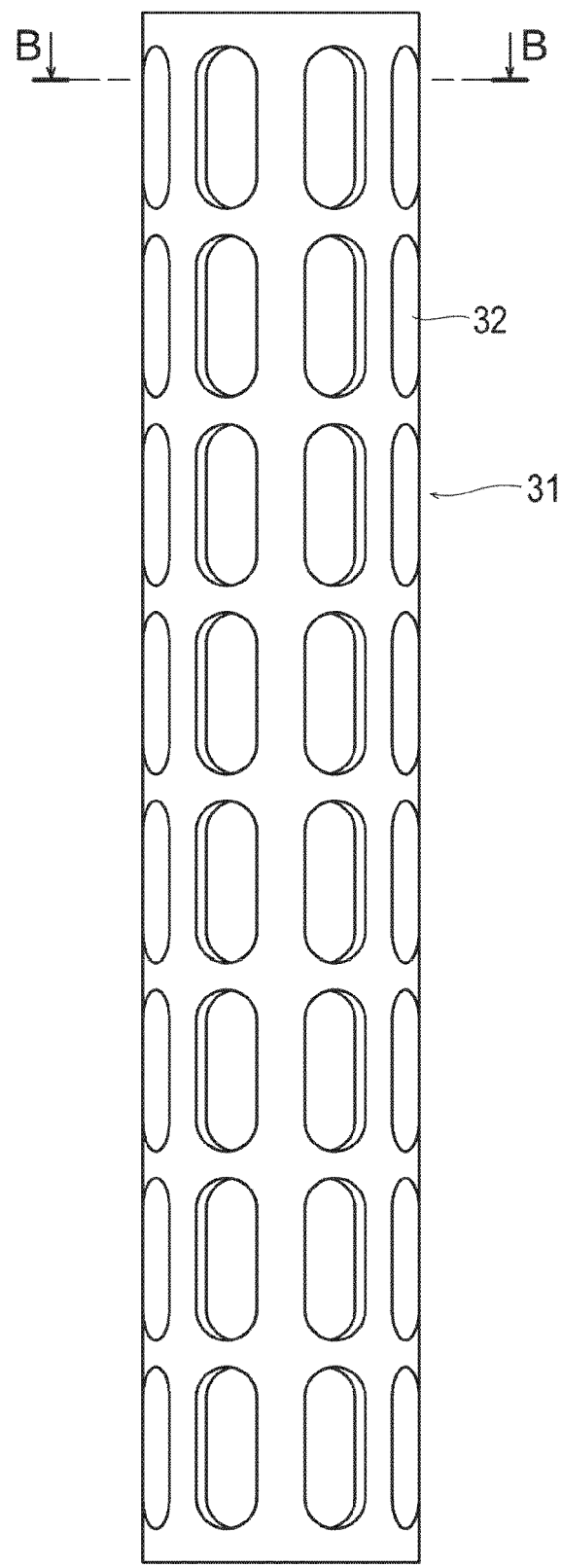
FIG. 5 is a front view illustrating an example of an inner tube used in the hollow fiber membrane-based oxygenator of external perfusion type according to the invention.
Figure 6:
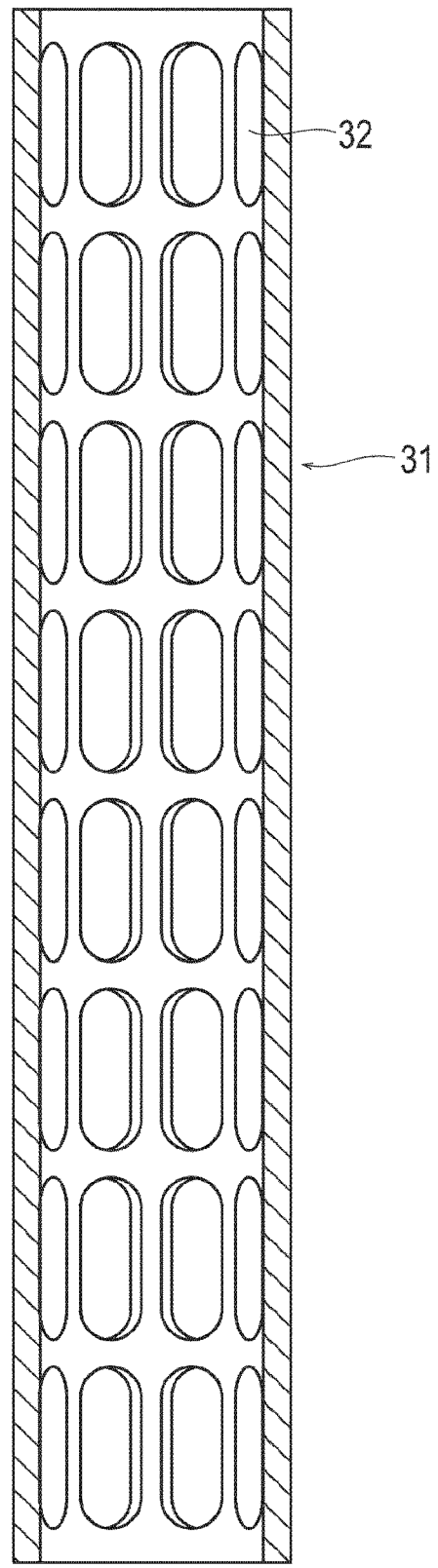
FIG. 6 is a central longitudinal sectional view of the inner tube illustrated in FIG. 5.
Figure 7:
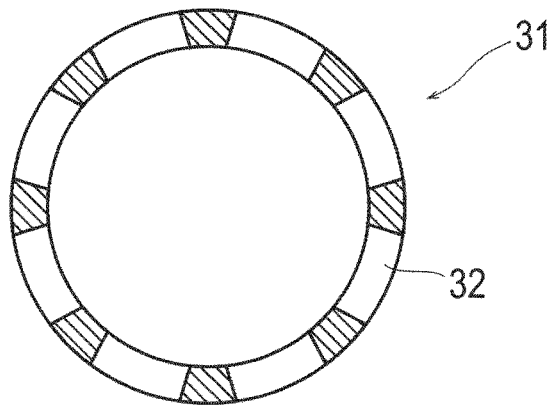
FIG. 7 is a cross-sectional view taken along line B-B of FIG. 5.

The inner tube 31 has the side surface provided with a large number of openings 32 for blood circulation. The openings 32 preferably have a large total area as long as required strength of the inner tube 31 is maintained. A preferred configuration that satisfies such a condition is illustrated in FIG. 5 (front view), FIG. 6 (central longitudinal sectional view of FIG. 5), and FIG. 7 (cross-sectional view taken along line B-B of FIG. 5). In this configuration, a plurality of (for example, 4 to 24) annular openings 32 (in the drawings, eight openings 32 in the longitudinal direction) is placed at regular intervals on the outer periphery of the inner tube 31, and a plurality of units of the openings 32 (in the drawings, eight units in the circumferential direction) is placed in the axial direction of the inner tube 31. Furthermore, the openings 32 may be shaped into a circle, polygon, or ellipse but are preferably shaped into an oval as illustrated in FIG. 5.

The inner cannula 35 is not particularly limited in shape and may be shaped into, for example, a cylinder or polygonal tube, or a tube having an elliptical cross-section. A cylinder is preferable. Furthermore, a distance between the distal opening of the inner cannula 35 and the first partition 25 is not particularly limited and may be similar to a distance employed in a known oxygenator. However, a preferable distance is about 20 to 50 mm. The inner cannula 35 is not particularly limited in inside diameter and may have a similar inside diameter to that of an inner tube used for a known oxygenator. However, a preferable inside diameter is about 10 to 30 mm.

The tubular hollow fiber membrane bundle 22 is not particularly limited in thickness and may have a thickness similar to that of a tubular hollow fiber membrane bundle used for a known oxygenator. However, the hollow fiber membrane bundle 22 preferably has a thickness of 5 to 35 mm and particularly preferably a thickness of 10 mm to 28 mm. Furthermore, the hollow fiber membranes 3 in the tubular space formed between the outer surface and the inner surface of the tubular hollow fiber membrane bundle 22 is not particularly limited in packing density and may be packed similarly to a known oxygenator. However, a preferable proportion of the hollow fiber membranes 3 is 40 to 85%, and a particularly preferable proportion is 45 to 80%. The tubular hollow fiber membrane bundle 22 may have an outside diameter similar to that of a hollow fiber membrane bundle used for a known oxygenator. However, the hollow fiber membrane bundle 22 preferably has an outside diameter of 30 to 170 mm, and more preferably an outside diameter of 70 mm to 130 mm. Such a configuration is employed as a gas exchange membrane.

The hollow fiber membrane bundle 22 is formed by winding hollow fiber membranes 3 around the inner tube 31. Specifically, a hollow fiber membrane bobbin is formed with the inner tube 31 as a core, both ends of the formed hollow fiber membrane bobbin are fixed by partitions 25 and 26, and then, both ends of the hollow fiber membrane bobbin are cut together with the inner tube 31 serving as a core, thereby forming the hollow fiber membrane bundle 22. Note that due to the cutting, the hollow fiber membranes 3 open at the outer surface of the partitions 25 and 26. A method for forming hollow fiber membranes is not limited to the above method, and a method similar to another known method for forming hollow fiber membranes or a modification of the known method is applicable.

Particularly, it is preferable to wind one hollow fiber membrane 3 or to wind a plurality of hollow fiber membranes 3 simultaneously around the inner tube 31 in such a manner that substantially parallel and adjacent hollow fiber membranes 3 are spaced at substantially regular intervals. This makes it possible to suppress uneven flows of blood more effectively. A distance between adjacent hollow fiber membranes 3 is preferably, but is not limited to, 1/10 to 1/1 of the outside diameter of the hollow fiber membranes 3. Furthermore, a distance between adjacent hollow fiber membranes 3 is preferably 30 to 200 μm.

Still further, it is preferable that the hollow fiber membrane bundle 22 is formed by winding one hollow fiber membrane 3 or winding a plurality of (preferably 2 to 16) hollow fiber membranes 3 simultaneously around the inner tube 31 in such a manner that all adjacent hollow fiber membranes 3 have a substantially constant interval and by operating a rotator for rotating the inner tube 31 and a winder for weaving the hollow fiber membranes 3 under conditions of the following Formula (1) when the hollow fiber membranes 3 are wound around the inner tube 31.

$$\text{TRAVERSE [mm/lot]} \cdot n(\text{INTEGER}) = \text{TRAVERSE WINDING WIDTH} \cdot 2 \pm (\text{FIBER OUTSIDE DIAMETER} + \text{INTERVAL}) \cdot \text{NUMBER OF WINDING FIBERS} \quad \text{FORMULA (1)}$$

With the above conditions, it is possible to reduce uneven flows of blood. The symbol "n", that is, a relation between the number of rotations of the winding rotator and the number of reciprocations of the winder, is not particularly limited but is typically 1 to 5 and more preferably 2 to 4.

Even in the hollow fiber membrane-based oxygenator 20, as illustrated in FIG. 2, a polymer layer 16 and an antithrombotic drug layer 18 are formed in this order (that is, in the order of the hollow fiber membranes, the polymer layer, and the antithrombotic drug layer) on at least one of the inner surface 3c' of the hollow fiber membranes 3 through which the oxygen-containing gas flows and the outer surface 3a' (the outer surface 3a' and the outer layer 3a according to circumstances) of the hollow fiber membranes 3 or the blood contact portion. Herein, the polymer layer 16 and the antithrombotic drug layer 18 are preferably disposed at least on the side where blood flows. In other words, the polymer layer 16 and the antithrombotic drug layer 18 are preferably formed at least on the outer surface 3a' of the hollow fiber membranes 3, and are more preferably formed on the outer surface 3a' of the hollow fiber membranes 3 in consideration of the effect of further improving gas permeability. A preferred embodiment (inside diameter, outside diameter, thickness, porosity, pore size, and the like) of hollow fiber membranes may be similar to one illustrated in FIG. 1 but is not particularly limited thereto.

Method for Manufacturing Oxygenator

Next, a method for manufacturing an oxygenator according to the invention will be described in detail. The manufacturing method is a method for manufacturing an oxygenator having a plurality of porous hollow fiber membranes for gas exchange, at least part of which includes polypropylene and each of which has an inner surface that forms a lumen and an outer surface, in which the method involves: preparing a coating solution containing at least one compound selected from the group consisting of dopamine, salt of dopamine, and oligomer of dopamine; and bringing the inner surface or the outer surface of the hollow fiber membranes into contact with the coating solution for less than ten hours while blowing oxygen gas in the coating solution to form a polymer layer containing a polymer of the compound on the inner surface or the outer surface.

In the manufacturing method of this embodiment, the first step is to prepare a coating solution containing at least one compound selected from the group consisting of dopamine, salt of dopamine, and oligomer of dopamine ((1) Coating Solution Preparation). The inner surface or the outer surface of the hollow fiber membranes is brought into contact with the coating solution for less than ten hours while oxygen gas is blown in the prepared coating solution ((2) Coating Solution Application). Each step will now be described.

(1) Coating Solution Preparation

This step is to prepare a coating solution containing at least one compound selected from the group consisting of dopamine, a salt thereof (salt of dopamine), and an oligomer thereof (oligomer of dopamine) (polymer layer forming compound). This coating solution is to be applied to an inner surface or an outer surface of hollow fiber membranes (hereinafter simply referred to as "surface of the hollow fiber membranes"). The coating solution contains a solvent and at least one compound selected from the group consisting of dopamine, salt of dopamine, and oligomer of dopamine (polymer layer forming compound).

The polymer layer forming compound is applied to the surface of the hollow fiber membranes in this step, and a polymer layer is formed as a homogeneous film in the following Step (2): Coating Solution Application. Accordingly, the hollow fiber membranes have a function of suppressing plasma leakage from one surface to the other surface (from the outer surface to the inner surface or from the inner surface to the outer surface) of the hollow fiber membranes (this is the reason that the hollow fiber membranes have excellent anti-plasma leakage properties. In addition, the hollow fiber membranes have a function of improving adhesion to an antithrombotic drug layer to be described in detail below (this is the reason that the hollow fiber membranes are capable of maintaining antithrombogenicity and anti-plasma leakage properties in long-term use). Herein, the polymer layer forming compound is selected from the group consisting of dopamine, salt of dopamine, and oligomer of dopamine. The salt of dopamine is not particularly limited, and examples thereof include dopamine hydrochloride (2-(3,4-dihydroxyphenyl) ethylamine hydrochloride). An example of the oligomer of dopamine includes polymers in which about 2 to 50 5,6-dihydroxyindoles are repeated. Among these examples, dopamine and a salt of dopamine are preferable, dopamine and dopamine hydrochloride are more preferable, and dopamine hydrochloride is particularly preferable from a perspective of further improving the anti-plasma leakage properties and the adhesion to the antithrombotic drug layer. That is, in a preferred embodiment of the invention, the compound is dopamine or a salt of dopamine. In a preferred embodiment of the invention, the compound is dopamine or dopamine hydrochloride. In a particularly preferred embodiment of the invention, the compound is dopamine hydrochloride.

The polymer layer forming compound may be either a commercial product or a synthetic product. The polymer layer forming compound is available from, for example, TOWA Yakuhin Co., Ltd., NACALAI TESQUE, INC., and Sigma-Aldrich Japan.

One kind of polymer layer forming compound may be used independently or two or more kinds may be used in combination.

The solvent used for preparing the coating solution is not particularly limited as long as it dissolves the polymer layer forming compound and is appropriately selected according to the type of the polymer layer forming compound. Specific examples of the solvent include buffer solutions such as phosphate buffer solution (PBS), carbonate buffer solution, Tris buffer solution, glycine buffer solution, and Tricine buffer solution; and HEPES buffer.

The coating solution is not particularly limited in concentration of polymer layer forming compound and preferably has a concentration of 0.1 mg/mL or more and 50 mg/mL or less and more preferably 0.5 mg/mL or more and 10 mg/mL or less from perspectives of improving permeability of the coating solution in lumina of the hollow fiber membranes, cost, and polymerization rate. In addition, the coating solution is not particularly limited in pH. The pH is preferably within a range of 5.0 to 10.0 and more preferably near neutral (for example, 6.0 to 8.0, particularly 6.5 to 7.5) from perspectives of operability and reactions of the polymer layer forming compound (particularly, the polymerization rate of dopamine).

In addition to the polymer layer forming compound and the solvent, the coating solution may optionally contain an additive. Examples of the additive include polyolefins, aliphatic hydrocarbons, inorganic fine particles, and water-soluble polymers.

(2) Coating Solution Application

In this step, the inner surface or the outer surface of the hollow fiber membranes is brought into contact with the coating solution for less than ten hours while oxygen gas is blown in the prepared coating solution, and the coating solution is applied to (covered on) the outer surface or the inner surface of the hollow fiber membranes. Since an embodiment (material, inside diameter, outside diameter, thickness, porosity, and pore size) of the hollow fiber membranes to which the coating solution is to be applied has been described in the chapter <Oxygenator>, the details thereof will not hereinafter be repeated.

Specifically, after assembling an oxygenator (for example, one having the structure illustrated in FIG. 1 or FIG. 3), the prepared coating solution is brought into contact with (or circulated through) at least one of the outer surface and the inner surface of the hollow fiber membranes, and oxygen gas is circulated directly or through openings of the hollow fiber membranes. This makes it possible to proceed with reactions (for example, oxidation and polymerization of dopamine) of the polymer layer forming compound on the outer surface or the inner surface (that is, the blood contact portion) of the hollow fiber membranes, and a coating film (polymer layer) containing polymers of the polymer layer forming compound is formed on the outer surface or the inner surface of the hollow fiber membranes. The coating solution may be applied to the hollow fiber membranes before the oxygenator is assembled. From perspectives of productivity and mass production, it is preferable that after the oxygenator (or the hollow fiber membrane bundle) is assembled, the coating solution is brought into contact with (or circulated through) at least one of the outer surface and the inner surface of the hollow fiber membranes while oxygen gas is circulated.

As mentioned above, a preferred embodiment of an oxygenator manufactured by the method according to the invention is of external perfusion type. Accordingly, it is preferable to apply the coating solution to the outer surface of the hollow fiber membranes. That is, in a preferred embodiment of the invention, the outer surface of the hollow fiber membranes is brought into contact with the coating solution containing the polymer layer forming compound, and oxygen gas is circulated from the lumina (inner surface) of the hollow fiber membranes through the openings.

Before the surface of the hollow fiber membranes is brought into contact with the coating solution, oxygen gas is preferably charged in the coating solution. This makes it possible to proceed with reactions (for example, oxidation and polymerization of dopamine) of the polymer layer forming compound more quickly and efficiently. Herein, conditions of charging oxygen gas are not particularly limited. However, it is preferable that the coating solution has an oxygen concentration (25° C.) of about 0.5 to 1.5 vol. %, particularly about 0.8 to 1.2 vol. %.

The method for bringing the surface of the hollow fiber membranes into contact with the coating solution is not particularly limited. For example, the hollow fiber membranes may be immersed in the coating solution, or the coating solution may be poured (charged) in the lumina of the hollow fiber membranes. Alternatively, the coating solution may be applied to the outer surface of the hollow fiber membranes. In a case where the coating solution is brought into contact with one surface of the hollow fiber membranes, for example, the hollow fiber membranes are immersed in the coating solution, and then, oxygen gas is circulated through the lumina of the hollow fiber membranes (according to this embodiment, a polymer layer is selectively formed on the outer surface of the hollow fiber membranes). Alternatively, a wire rod having an inside diameter substantially equal to that of the lumina of the hollow fiber membranes is inserted into the lumina of the hollow fiber membranes, or both ends of the hollow fiber membranes are closed to prevent the coating solution from entering the lumina, and then, the hollow fiber membranes are brought into contact with the coating solution (according to this embodiment, a polymer layer is selectively formed on the outer surface of the hollow fiber membranes). Alternatively, after the outer surface of the hollow fiber membranes is sealed with a film or the like, the hollow fiber membranes are brought into contact with the coating solution (according to this embodiment, a polymer layer is selectively formed on the inner surface of the hollow fiber membranes). Alternatively, the hollow fiber membranes are brought into contact with a coating solution while the lumina of the hollow fiber membranes are filled with a nonpolar solvent in advance.

Next, oxygen gas is blown onto the coating solution. Accordingly, the polymer layer forming compound in the coating solution reacts (for example, dopamine is oxidized and polymerized), and a reactant of the polymer layer forming compound (such as polydopamine) is formed and deposited on the surface of the hollow fiber membranes, thereby forming a polymer layer. Herein, a time for contacting (blowing) the oxygen gas is less than ten hours. If the contact between the coating solution and the hollow fiber membranes lasts for ten hours or more, the reactions of the polymer layer forming compound (for examples, oxidation and polymerization of dopamine) excessively proceed, the layer (for example, a dopamine polymer layer) becomes thick, which excessively decreases gas exchange performance (gas transmission rate). The resulting hollow fiber membranes would be less suitable for an oxygenator. In addition, it is also disadvantageous and not preferable from a cost perspective. A time for contacting (blowing) the oxygen gas is preferably 8 hours or less, more preferably less than 6 hours, still more preferably 5 hours or less, and particularly preferably 4 hours or less from perspectives of adhesion to the hollow fiber membranes and the antithrombotic drug layer (to be described in detail), gas exchange performance (gas transmission rate), and balance between the adhesion and the performance. The lower limit of the time for contacting (blowing) the oxygen gas is preferably more than 15 minutes, more preferably more than 30 minutes, still more preferably 40 minutes or more, still more preferably 60 minutes or more, and particularly preferably 120 minutes or more from perspectives of adhesion to the hollow fiber membranes and the antithrombotic drug layer to be described in detail. Therefore, the time for contacting (blowing) the oxygen gas is preferably more than 15 minutes and less than 10 hours, more preferably more than 30 minutes and 8 hours or less, still more preferably 40 minutes or more and less than 6 hours, still more preferably 60 minutes or more and 5 hours or less, and particularly preferably 120 minutes or more and 4 hours or less. Within these ranges of contacting (blowing) time, the hollow fiber membranes and the antithrombotic drug layer are adhered to each other more firmly via the polymer layer while ensuring sufficient anti-plasma leakage properties and gas exchange performance (gas transmission rate).

A method for blowing oxygen gas is not particularly limited as long as the above reactions proceed efficiently. For example, one end of the hollow fiber membranes may be connected to an oxygen gas tank, and oxygen gas is blown into the lumina of the hollow fiber membranes. Alternatively, oxygen gas is bubbled into the coating solution to bring the polymer layer forming compound into contact with the oxygen gas.

Note that the inner surface of the hollow fiber membranes may be brought into contact with the coating solution with the lumina of the hollow fiber membranes being under a predetermined negative pressure. According to this method, the coating solution is brought into contact with the surface of the hollow fiber membranes (particularly, the lumina of the hollow fiber membranes) more uniformly and reliably. In this embodiment, the negative pressure is not particularly limited in degree, but the lumina of the hollow fiber membranes may be at a negative pressure of 50 hPa or more and 150 hPa or less, and preferably 50 hPa or more and 100 hPa or less. As an example of a method for evacuating the lumina of the hollow fiber membranes to a negative pressure, a vacuum pump (such as a diaphragm pump) is airtightly connected to one end of the hollow fiber membranes and then operated, but the method is not particularly limited thereto. Herein, the "degree of negative pressure (atmospheric pressure)" is a value of the standard pressure of a vacuum pump.

In addition to pure oxygen gas, the oxygen gas may be a mixed gas containing oxygen gas. Preferably, the oxygen gas is pure oxygen gas (amount of other gases contained: each substantially 0% by volume (less than 5% by volume with respect to the total volume). Herein, in a case where a mixed gas is used, other gases that may be used are not particularly limited unless the effects according to the invention are impaired. For example, an inert gas such as nitrogen gas, argon gas, and helium gas is applicable. From a perspective of efficient process of the reactions, an amount of other gases contained is preferably more than 0 vol. % and less than 50 vol. % and more preferably more than 0 vol. % and less than 20 vol. % with respect to the total amount (volume) of the mixed gas to be circulated.

Other conditions of blowing the oxygen gas are not particularly limited. Specifically, a blowing temperature is preferably 10 to 60° C., and more preferably 25 to 40° C. Furthermore, a blowing rate of the oxygen gas is preferably 0.05 to 0.7 L/min, and more preferably 0.25 to 0.5 L/min. Under such conditions, a sufficient amount of the oxygen gas is supplied to the polymer layer forming compound, thereby sufficiently proceeding the reactions of the polymer layer forming compound (such as oxidation and polymerization of dopamine).

Accordingly, the polymer layer forming compound reacts to form a layer (for example, a dopamine polymer layer) on the surface of the hollow fiber membranes. Optionally, this state may be retained after blowing the oxygen gas. This operation further proceeds the reactions of the polymer layer forming compound and makes it possible to form the polymer layer efficiently on the surface of the hollow fiber membranes. Herein, retaining conditions are not particularly limited. Specifically, a retaining temperature is preferably 10 to 60° C., and more preferably 25 to 40° C. A time of retaining is preferably 30 minutes to 24 hours, and preferably 1 to 12 hours. Under such conditions, it is possible to proceed the reactions of the polymer layer forming compound more sufficiently, which enables formation of the polymer layer more efficiently on the surface of the hollow fiber membranes. This retaining operation may be performed in the air or an inert gas atmosphere.

After that, the coating film is optionally washed and dried. The washing is not particularly limited and may be performed with, for example, water or an alcohol solvent (such as ethanol). Accordingly, an unreacted polymer layer forming compound is removed. Examples of the drying include, but are not particularly limited to, natural drying, vacuum drying, and high-temperature drying at normal pressure.

In this manner, the polymer layer is formed on the surface of the hollow fiber membranes. The polymer layer is not particularly limited in thickness (thickness after drying) and preferably has a thickness of 10 to 500 nm, more preferably 100 to 400 nm, and still more preferably 150 to 300 nm. With a thickness of 10 nm or more, the polymer layer has sufficient adhesion to the surface of the hollow fiber membranes and the antithrombotic drug layer and also has sufficient anti-plasma leakage properties. With a thickness of 500 nm or less, the polymer layer is prevented from deteriorating in gas exchange performance. Herein, the thickness of the polymer layer employs a value measured by the following procedure. That is, thermogravimetry (TG) is performed to measure a change in mass of coated polymers, and the mass is divided by a density of the polymers to calculate a volume, followed by dividing the volume by a surface area. In a case where the polymer layer includes polydopamine (PDA) (the polymer layer is a polydopamine layer), TG is performed to measure a change in mass of coated PDA, and the mass is divided by a density (1.00 g/cm$^3$) of the PDA to calculate a volume, and a value obtained by dividing the volume by a surface area is regarded as the thickness of the polymer layer.

The polymer layer is formed on the surface of the hollow fiber membranes by Steps (1) and (2). The method for manufacturing an oxygenator according to this embodiment may optionally include other steps in addition to Steps (1) and (2). Other steps include the following Step (3), Antithrombotic Drug Layer Formation. The step is preferably performed after Steps (1) and (2).

(3) Antithrombotic Drug Layer Formation

This step is to form an antithrombotic drug-containing coat (antithrombotic drug layer) on the polymer layer. In an embodiment, an aqueous coating solution containing an antithrombotic drug is prepared, and the aqueous coating solution is applied to the polymer layer formed on the outer surface or the inner surface of the hollow fiber membranes in Step (2). As described above, the polymer layer and the antithrombotic drug layer are preferably formed on the outer surface of the hollow fiber membranes. That is, in a preferred embodiment of the invention, the manufacturing method of the invention further involves forming the polymer layer on the outer surface of the hollow fiber membranes and forming an antithrombotic drug layer having an antithrombotic drug on the polymer layer. A method for forming an antithrombotic drug and antithrombotic drug layer (coat) is not particularly limited and may appropriately employ a known method.

The antithrombotic drug is a compound that imparts antithrombogenicity to the oxygenator when being applied to the polymer layer formed on the surface of the hollow fiber membranes, or the blood contact portion (for example, the outer surface of the hollow fiber membranes).

Any antithrombotic drug can be employed without limitation as long as the drug has antithrombogenicity and biocompatibility. Particularly, from a perspective of excellent properties, the antithrombotic drug preferably has an alkoxyalkyl (meth)acrylate-derived unit represented by the following Formula (1). That is, in a preferred embodiment of the invention, the antithrombotic drug has a unit (1) represented by the following Formula (1).

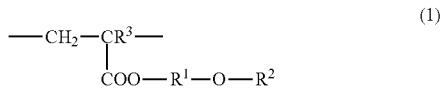

(1)

In Formula (1), $R^1$ is a $C_{1-4}$ alkylene group; $R^2$ is a $C_{1-4}$ alkyl group; and $R^3$ is a hydrogen atom or a methyl group.

The compound having the unit represented by Formula (1) is excellent in antithrombotic biocompatibility (has excellent effects of suppressing and preventing adhesion/attachment of platelets and suppressing and preventing activation of platelets), particularly, excellent effects of suppressing and preventing adhesion/attachment of platelets. Accordingly, using the compound having the unit makes it possible to manufacture an oxygenator having excellent antithrombotic biocompatibility (excellent effects of suppressing and preventing adhesion/attachment of platelets and suppressing and preventing activation of platelets), particularly, excellent effects of suppressing and preventing adhesion/attachment of platelets.

Herein, "(meth)acrylate" represents "acrylate and/or methacrylate". In other words, the term "alkoxyalkyl (meth) acrylate" includes not only "alkoxyalkyl acrylate or alkoxyalkyl methacrylate" but also "alkoxyalkyl acrylate and alkoxyalkyl methacrylate".

In Formula (1), $R^1$ is a $C_{1-4}$ alkylene group. Examples of the $C_{1-4}$ alkylene group include, but are not particularly limited to, linear or branched alkylene groups such as methylene group, ethylene group, trimethylene group, tetramethylene group, and propylene group. Among these examples, ethylene group and propylene group are preferable, and ethylene group is particularly preferable in consideration of further improving antithrombogenicity and biocompatibility. $R^2$ is a $C_{1-4}$ alkyl group. Examples of the $C_{1-4}$ alkyl group include, but are not particularly limited to, linear or branched alkyl groups such as methyl group, ethyl group, propyl group, isopropyl group, butyl group, isobutyl group, sec-butyl group, and tert-butyl group. Among these examples, methyl group and ethylene group are preferable, and methyl group is particularly preferable in consideration of further improving antithrombogenicity and biocompatibility. $R^3$ is a hydrogen atom or a methyl group.

In a case where the antithrombotic drug has two or more kinds of alkoxyalkyl (meth)acrylate-derived units, the units may be the same or different.

Specific examples of the alkoxyalkyl (meth)acrylate include methoxymethyl acrylate, methoxyethyl acrylate, methoxypropyl acrylate, ethoxymethyl acrylate, ethoxyethyl acrylate, ethoxypropyl acrylate, ethoxybutyl acrylate, propoxymethyl acrylate, butoxyethyl acrylate, methoxybutyl acrylate, methoxymethyl methacrylate, methoxyethyl methacrylate, ethoxymethyl methacrylate, ethoxyethyl methacrylate, propoxymethyl methacrylate, and butoxyethyl methacrylate. Among these examples, methoxyethyl (meth) acrylate and methoxybutyl acrylate are preferable, and methoxyethyl acrylate (MEA) is particularly preferable from a perspective of further improving antithrombogenicity and biocompatibility. In other words, the antithrombotic drug is preferably polymethoxyethyl acrylate (PMEA). One of these examples of the alkoxyalkyl (meth)acrylate may be used independently or two or more kinds may be used in combination.

The antithrombotic drug according to the invention preferably has an alkoxyalkyl (meth)acrylate-derived unit and may be a polymer (homopolymer) having one kind or two or more kinds of alkoxyalkyl (meth)acrylate-derived units. Alternatively, the antithrombotic drug may be a polymer (copolymer) having one kind or two or more kinds of alkoxyalkyl (meth)acrylate-derived units and one kind or two or more kinds of monomer-derived units (other units) copolymerizable with the alkoxyalkyl (meth)acrylate. In a case where the antithrombotic drug according to the invention has two or more units, the polymer (copolymer) is not particularly limited in structure and may be any of a random copolymer, alternating copolymer, periodic copolymer, and block copolymer. A terminal of the polymer is not particularly limited and is appropriately determined depending on the type of a raw material to be used and is typically a hydrogen atom.

Herein, in a case where the antithrombotic drug according to the invention has another unit in addition to the alkoxyalkyl (meth)acrylate-derived unit, monomers copolymerizable with the alkoxyalkyl (meth)acrylate (copolymerizable monomers) is not particularly limited. Examples of the copolymerizable monomers include methyl acrylate, ethyl acrylate, propyl acrylate, butyl acrylate, 2-ethylhexyl acrylate, methyl methacrylate, ethyl methacrylate, propyl methacrylate, butyl methacrylate, 2-ethylhexyl methacrylate, hexyl acrylate, hexyl methacrylate, ethylene, propylene, acrylamide, N, N-dimethylacrylamide, N, N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N, N-dimethylmethacrylamide, N, N-diethylmethacrylamide, aminomethyl methacrylate, aminoethyl methacrylate, diaminomethyl methacrylate, and diaminoethyl methacrylate. Among these examples, the copolymerizable monomers is preferably one having no hydroxyl group or cationic group in a molecule. The copolymer may be any of a random copolymer, block copolymer, and graft copolymer and is synthesized by a known method such as radical polymerization, ion polymerization, and polymerization using a macromer. Herein, a proportion of units derived from the copolymerizable monomers in all the units of the copolymer is not particularly limited. However, in consideration of antithrombogenicity, biocompatibility, and the like, the units derived from the copolymerizable monomers (other units) preferably account for more than 0 mol % and 50 mol % or less of all the units of the copolymer. A proportion more than 50 mol % may deteriorate the effects of the alkoxyalkyl (meth)acrylate.

A weight average molecular weight of the antithrombotic drug herein is not particularly limited but is preferably 80,000 or more. In the method for manufacturing an oxygenator according to this embodiment, the antithrombotic drug is applied to the polymer layer formed on the outer surface or the inner surface of the hollow fiber membranes in the form of an aqueous coating solution. Therefore, from a perspective of easily preparing a desired aqueous coating solution, the antithrombotic drug preferably has a weight average molecular weight less than 800,000. Such a range suppresses aggregation or precipitation of the compound in an antithrombotic drug-containing solution and enables preparation of a stable aqueous coating solution. Furthermore, a weight average molecular weight of the antithrombotic drug is preferably more than 200,000 and less than 800,000, more preferably 210,000 or more and 600,000 or less, still more preferably 220,000 or more and 500,000 or less, and particularly preferably 230,000 or more and 450,000 or less.

Herein, the "weight average molecular weight" is measured by gel permeation chromatography (GPC) using polystyrene as a standard substance and tetrahydrofuran (THF) as a mobile phase. Specifically, a polymer of interest is dissolved in THF to prepare a 10 mg/ml solution. GPC column LF-804 available from Shodex is attached to GPC system LC-20 available from Shimadzu Corporation, and THF is allowed to flow as a mobile phase through the column. Using polystyrene as a standard substance, the polymer of interest in the prepared polymer solution is measured by GPC. A calibration curve is prepared using the standard polystyrene. Based on this curve, a weight average molecular weight of the polymer of interest is calculated.

It is inferred that an increase of molecular weight of the antithrombotic drug reduces an amount of polymers having a relatively low molecular weight contained in a coat, which leads to suppression and prevention of the polymers having a relatively low molecular weight from being transferred to blood. Accordingly, with a weight average molecular weight falling within the above ranges, the antithrombotic drug suppresses and prevents a transfer of a coat (particularly, polymers having a low molecular weight) to blood more effectively. It is also preferable from a perspective of antithrombogenicity and biocompatibility. In addition, the "polymers having a low molecular weight" herein refers to polymers having a weight average molecular weight less than 60,000. A method for measuring a weight average molecular weight is as described above.

The antithrombotic drug containing the alkoxyalkyl (meth)acrylate-derived unit represented by Formula (1) is produced by a known method. As a preferred example, specifically, alkoxyalkyl (meth)acrylate represented by the following Formula (2) and one or more optionally-added monomers copolymerizable with the alkoxyalkyl (meth) acrylate (copolymerizable monomers) are stirred together with a polymerization initiator in a polymerization solvent to prepare a monomer solution, followed by heating the monomer solution to (co)polymerize the alkoxyalkyl (meth)acrylate or (co)polymerize the alkoxyalkyl (meth)acrylate and the optionally-added copolymerizable monomers.

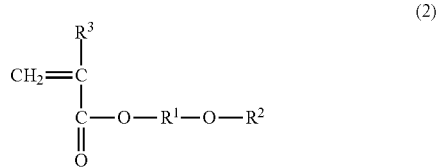

(2)

The substituents $R^1$, $R^2$, and $R^3$ in Formula (2) are similar to those defined in Formula (1) and will not hereinafter be described.

The polymerization solvent used in preparing the monomer solution is not particularly limited as long as the solvent dissolves the alkoxyalkyl (meth)acrylate represented by Formula (2) and the optionally-added copolymerizable monomers. Examples of the polymerization solvent include aqueous solvents such as water, alcohols (for example, methanol, ethanol, propanol, and isopropanol), and polyethylene glycols; aromatic solvents such as toluene, xylene, and tetralin; and halogen-based solvents such as chloroform, dichloroethane, chlorobenzene, dichlorobenzene, and trichlorobenzene. Among these examples, methanol is preferable in consideration of dissolubility of alkoxyalkyl (meth) acrylate and obtainability of polymers having a weight average molecular weight as described above.

The monomer solution is not particularly limited in concentration of monomers. However, a relatively high concentration of monomers causes an increase in weight average molecular weight of the obtained antithrombotic drug. Therefore, in consideration of obtainability of polymers having a weight average molecular weight as described above, the monomer solution preferably has a concentration of monomers less than 50 mass %, and more preferably 15 mass % or more and less than 50 mass %. Furthermore, the monomer solution more preferably has a concentration of monomers of 20 mass % or more and 48 mass % or less, and particularly preferably 25 mass % or more and 45 mass % or less. In a case where two or more monomers are used, the concentration of monomers represents the total concentration of the monomers employed.

The polymerization initiator is not particularly limited, and a known polymerization initiator may be used. The polymerization initiator is preferably a radical polymerization initiator from a perspective of excellent polymerization stability. Specific examples of the radical polymerization initiator include persulfates such as potassium persulfate (KPS), sodium persulfate, and ammonium persulfate; peroxides such as hydrogen peroxide, t-butyl peroxide, and methyl ethyl ketone peroxide; and azo compounds such as azobisisobutyronitrile (AIBN), 2,2'-azobis (4-methoxy-2,4-dimethylvaleronitrile), 2,2'-azobis (2,4-dimethylvaleronitrile), 2,2'-azobis [2-(2-imidazoline-2-yl) propane] dihydrochloride, 2,2'-azobis [2-(2-imidazoline-2-yl) propane] disulfate dihydrate, 2,2'-azobis (2-methylpropionamidine) dihydrochloride, 2,2'-azobis [N-(2-carboxyethyl)-2 methylpropionamidine)] hydrate, 3-hydroxy-1,1-dimethylbutyl peroxyneodecanoate, α-cumyl peroxyneodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl) peroxydicarbonate, di(sec-butyl) peroxydicarbonate, and azobiscyanovaleric acid. Alternatively, for example, a reducing agent such as sodium sulfite, sodium bisulfite, and ascorbic acid may be used in combination with the radical polymerization initiator as a redox initiator. An amount of the polymerization initiator to be mixed is preferably 0.0001 to 1 mol %, more preferably 0.001 to 0.8 mol %, and particularly preferably 0.01 to 0.5 mol % with respect to the total amount of the monomers (alkoxyalkyl (meth)acrylate and the optionally-added copolymerizable monomers; hereinafter, the same shall apply). Alternatively, an amount of the polymerization initiator to be mixed is preferably 0.005 to 2 parts by mass and more preferably 0.05 to 0.5 parts by mass with respect to 100 parts by mass of the monomers (or with respect to all kinds of monomers when using multiple kinds of monomers). Mixing such an amount of the polymerization initiator enables more efficient production of polymers having a desired weight average molecular weight.

The polymerization initiator may be mixed as it is with the monomers and the polymerization solvent. Alternatively, the polymerization initiator may be mixed with the monomers and the polymerization solvent by being dissolved in another solvent in advance. In the latter case, an example of the other solvent includes, but is not particularly limited to, a solvent similar to the polymerization solvent as long as it dissolves the polymerization initiator. The other solvent may be the same as or different from the polymerization solvent but is preferably the same as the polymerization solvent in consideration of polymerization controllability. The polymerization initiator in the other solvent in this case is not particularly limited in concentration. In consideration of mixability and the like, an amount of the polymerization initiator to be added is preferably 0.1 to 10 parts by mass, more preferably 0.15 to 5 parts by mass, and still more preferably 0.2 to 1.8 parts by mass with respect to 100 parts by mass of the other solvent.

Next, the monomer solution is heated to (co)polymerize alkoxyalkyl (meth)acrylate or alkoxyalkyl (meth)acrylate and the other monomers. The polymerization method herein may employ any known method such as radical polymerization, anionic polymerization, and cationic polymerization, but it is preferable to employ radical polymerization using radicals that are easy to produce.

Polymerization conditions are not particularly limited as long as the monomers (alkoxyalkyl (meth)acrylate or alkoxyalkyl (meth)acrylate and the copolymerizable monomers) are polymerized. Specifically, a polymerization temperature is preferably 30 to 60° C., and more preferably 40 to 55° C. A time of polymerization is preferably 1 to 24 hours, and preferably 3 to 12 hours. Such conditions enable efficient production of polymers having a high molecular weight as described. In addition, such conditions effectively suppress and prevent gelation in the polymerization, which enables high production efficiency.

Furthermore, a chain transfer agent, a polymerization rate adjusting agent, a surfactant, and other additives may be optionally used in the polymerization.

An atmosphere during polymerization reactions is not particularly limited. The polymerization may be performed, for example, in the air or an atmosphere of inert gas such as nitrogen gas and argon gas. During the polymerization reactions, the reaction solution may be stirred.

Polymers after the polymerization are purified by a typical purification method such as reprecipitation, dialysis, ultrafiltration, and extraction. Among these examples, the purification is preferably performed by reprecipitation because it is possible to obtain (co)polymers suitable for preparation of an aqueous coating solution. Note that ethanol is preferably used as a poor solvent for the reprecipitation.

The polymers after the purification are dried by any method such as freeze drying, vacuum drying, spray drying, and heat drying but are preferably dried by freeze drying or vacuum drying from a perspective that physical properties of the polymers are less affected.

As described above, in an embodiment of the invention, an antithrombotic drug-containing aqueous coating solution is prepared, and the aqueous coating solution is applied to the polymer layer formed on the outer surface or the inner surface of the hollow fiber membranes in Step (2) to form an antithrombotic drug-containing coat (antithrombotic drug layer) on the polymer layer.

Aqueous Coating Solution Preparation

Next, a method for preparing the aqueous coating solution according to the invention will be described.

A solvent used for preparing the antithrombotic drug-containing solution (aqueous coating solution) is not particularly limited as long as the solvent enables preparation of the aqueous coating solution by appropriately dispersing the antithrombotic drug. From a perspective of preventing permeation of the aqueous coating solution more effectively to the outer surface or the inner surface (the surface on the side where the oxygen-containing gas flows) of the pores of the hollow fiber membranes, the solvent preferably contains water. Herein, water is preferably pure water, ion-exchanged water, or distilled water. Among these examples, distilled water is particularly preferable.

Non-water solvent to be used for preparing the aqueous coating solution is not particularly limited. In consideration of controllability of dispersibility or the like of the antithrombotic drug, methanol and acetone are preferable. One of these examples of the non-water solvent may be used independently or two or more kinds may be mixed and used as a mixture. Among these examples, methanol is preferable in consideration of further controllability of dispersibility or the like of the antithrombotic drug. In other words, the solvent preferably includes water and methanol. Herein, a mixing ratio of water to methanol is not particularly limited. In consideration of dispersibility of the antithrombotic drug and controllability of mean particle size of colloids, the mixing ratio (mass ratio) of water:methanol is preferably 6 to 32:1, and more preferably 10 to 25:1. That is, the solvent preferably includes water and methanol at a mixing ratio (mass ratio) of 6 to 32:1, and more preferably at a mixing ratio (mass ratio) of 10 to 25:1.

As described above, when the aqueous coating solution is prepared using a mixed solvent of water and a non-water solvent, the order of adding the solvent (for example, water and methanol) and the antithrombotic drug is not particularly limited, but it is preferable to prepare the aqueous coating solution by the following procedure. That is, the aqueous coating solution is preferably prepared by adding the antithrombotic drug to a non-water solvent (preferably methanol) to prepare an antithrombotic drug-containing solution, and then, adding the antithrombotic drug-containing solution to water. This procedure easily disperses the antithrombotic drug. In addition, this procedure creates such advantages that colloids with a uniform particle size are formed and that it becomes easy to form a uniform coat.

In the procedure, a rate of adding the antithrombotic drug-containing solution to water is not particularly limited, but it is preferable to add the antithrombotic drug-containing solution to water at a rate of 5 to 100 g/min.

A stirring time and stirring temperature in the preparation of the aqueous coating solution are not particularly limited. From perspectives of easily forming colloids with a uniform particle size and uniformly dispersing the colloids, the antithrombotic drug-containing solution is preferably stirred for 1 to 30 minutes, and more preferably 5 to 15 minutes, after being added to water. Furthermore, the stirring temperature is preferably 10 to 40° C., and more preferably 20 to 30° C.

The antithrombotic drug in the aqueous coating solution is not particularly limited in concentration and preferably has a concentration of 0.01 mass % or more from a perspective of easily increasing an amount of coating. Furthermore, from the above perspective, the antithrombotic drug in the aqueous coating solution preferably has a concentration of 0.05 mass % or more, and particularly preferably 0.1 mass % or more. The concentration of the antithrombotic drug in the aqueous coating solution is not particularly limited by a ceiling but is preferably 0.3 mass % or less, and more preferably 0.2 mass % or less in consideration of, for example, formability of a coat and reduction in uneven coating. In addition, a concentration within such ranges also suppresses a decrease in gas exchange performance due to an excessively thick coat of the antithrombotic drug.

Aqueous Coating Solution Application

Next, the prepared aqueous coating solution is applied to (covered on) the polymer layer formed on the outer surface or the inner surface of the hollow fiber membranes in Step (2). Specifically, after assembling an oxygenator (for example, one having the structure illustrated in FIG. 1 or FIG. 3), the polymer layer is formed on the inner surface or the outer surface of the hollow fiber membranes, and the aqueous coating solution is brought into contact with the polymer layer (or circulated through the surface where the polymer layer is formed), whereby the polymer layer (preferably the polymer layer formed on the outer surface of the hollow fiber membranes (that is, the blood contact portion)) is covered with the antithrombotic drug. Accordingly, an antithrombotic drug layer is formed on the polymer layer. The application of the aqueous coating solution to the hollow fiber membranes may be performed before the assembly of the oxygenator.

A method for bringing the polymer layer into contact with the antithrombotic drug-containing aqueous coating solution is not particularly limited and may employ a method known in the art such as filling and dip coating (immersion). Among these examples, filling is preferable in order to increase an amount of the antithrombotic drug to be coated.

When employing filling as a method for bringing the antithrombotic drug-containing aqueous coating solution into contact with the polymer layer, a filling volume of the aqueous coating solution is preferably 50 g/m$^2$ or more and more preferably 80 g/m$^2$ or more with respect to the membrane area (m$^2$) of the hollow fiber membranes. With a filling volume of 50 g/m$^2$ or more, it is possible to form a coat containing a sufficient amount of the antithrombotic drug (antithrombotic drug layer) on the surface of the hollow fiber membranes. The filling volume is not particularly limited by a ceiling but is preferably 200 g/m$^2$ or less, and more preferably 150 g/m$^2$ or less with respect to the membrane area (m$^2$) of the hollow fiber membranes.

Herein, the "membrane area" refers to an area of the outer surface of the hollow fiber membranes and is calculated by multiplying the outside diameter, pi, the number, and the effective length of the hollow fiber membranes.

A time period for bringing the polymer layer into contact with the antithrombotic drug-containing aqueous coating solution is also not particularly limited but is preferably 0.5 minutes or more and 70 minutes or less and more preferably 1 minute or more and 5 minutes or less in consideration of, for example, an amount of coating, formability of a coating film, and the effect of reducing uneven coating. In addition, a temperature for contacting the aqueous coating solution and the polymer layer (a temperature for circulating the aqueous coating solution) is preferably 5 to 40° C. and more preferably 15 to 30° C. in consideration of, for example, an amount of coating, formability of a coating film, and the effect of reducing uneven coating.

After the contact with the aqueous coating solution, the coating film is dried, whereby a covering containing the antithrombotic drug (antithrombotic drug layer) according to the invention is formed on the polymer layer. Herein, drying conditions are not particularly limited as long as the covering containing the antithrombotic drug (antithrombotic drug layer) is formed on the polymer layer. Specifically, a drying temperature is preferably 5 to 50° C., and more preferably 15 to 40° C. A drying time is preferably 60 to 300 minutes, and more preferably 120 to 240 minutes. Alternatively, the coating film may be dried by circulating a gas through the hollow fiber membranes continuously or stepwise at a temperature of preferably 5 to 40° C., and more preferably 15 to 30° C. Herein, the gas is not particularly limited in type as long as the gas has no influence on the coating film and is capable of drying the coating film. Specific examples of the gas include air and an inert gas such as nitrogen gas or argon gas. Furthermore, an amount of the gas to be circulated is not particularly limited as long as the gas sufficiently dries the coating film and is preferably 5 to 150 L and more preferably 30 to 100 L.

Through the above steps, it is possible to obtain an oxygenator in which a polymer layer and an antithrombotic drug layer are formed on the inner or the outer surface of the hollow fiber membranes. Therefore, the manufacturing method according to this embodiment provides an oxygenator having both desired antithrombogenicity and anti-plasma leakage properties. In addition, the oxygenator manufactured by the method according to this embodiment maintains the antithrombogenicity and the anti-plasma leakage properties even after a month of use or more (that is, the oxygenator is also excellent in durability (maintainability of the antithrombogenicity and the anti-plasma leakage properties). Accordingly, an oxygenator manufactured by the method according to this embodiment of the invention is preferably used not only as an oxygenator for normal surgery but also as a pulmonary support for a patient with a serious disease.

EXAMPLES

The effects of the invention will be described with reference to the following Examples. Note that the technical scope of the invention is not limited to the following Examples. In the following Examples, unless otherwise specified, each operation was performed at room temperature (25° C.). Unless otherwise specified, "%" and "parts" represent "% by mass" and "parts by mass", respectively.

Examples 1 to 4

Dopamine hydrochloride (available from Sigma-Aldrich Japan) was added to a PBS solution (composition: 8 g/L NaCl, 0.2 g/L KCl, 1.15 g/L Na$_2$HPO$_4$, 0.2 g/L KH$_2$PO$_4$, pH 7.4) to prepare a solution having a dopamine hydrochloride concentration of 2 mg/mL. This mixed solution was placed in a sealed container, and oxygen gas was charged in the solution until an oxygen concentration (25° C.) became 1.12 vol. %, thereby preparing a DA/PBS solution 1 (pH 7.4).

Polypropylene porous hollow fiber membranes 51 (outside diameter: 170 μm, inside diameter: 112 μm, thickness: 29 μm, pore size: 0.05 μm, porosity: 30 vol. %, membrane area: 0.05 m$^2$) were immersed in the prepared DA/PBS solution 1. Next, one end of the hollow fiber membranes 51 was potted in a urethane resin inside a vinyl chloride tube and connected to an oxygen gas tank with an air hose and a joint. Oxygen gas was blown from the oxygen gas tank into the lumina of the hollow fiber membranes 51 at a rate of 0.3 L/min for 240 minutes (Example 1), 120 minutes (Example 2), 60 minutes (Example 3), and 30 minutes (Example 4), and then, the status of the hollow fiber membranes 51 were retained at 37° C. for one hour. Accordingly, dopamine was oxidized and polymerized to form a dopamine polymer layer (polymer layer) on the surface of the hollow fiber membranes (retained hollow fiber membranes 1 to 4). Excluding the status-retention at 37° C. for one hour, each operation was performed at 25° C. The retained hollow fiber membranes 1 to 4 were taken out from the DA/PBS solution 1, washed with RO water, and naturally dried at room temperature (25° C.) to obtain coated hollow fiber membranes 1 to 4.

Figure 8:
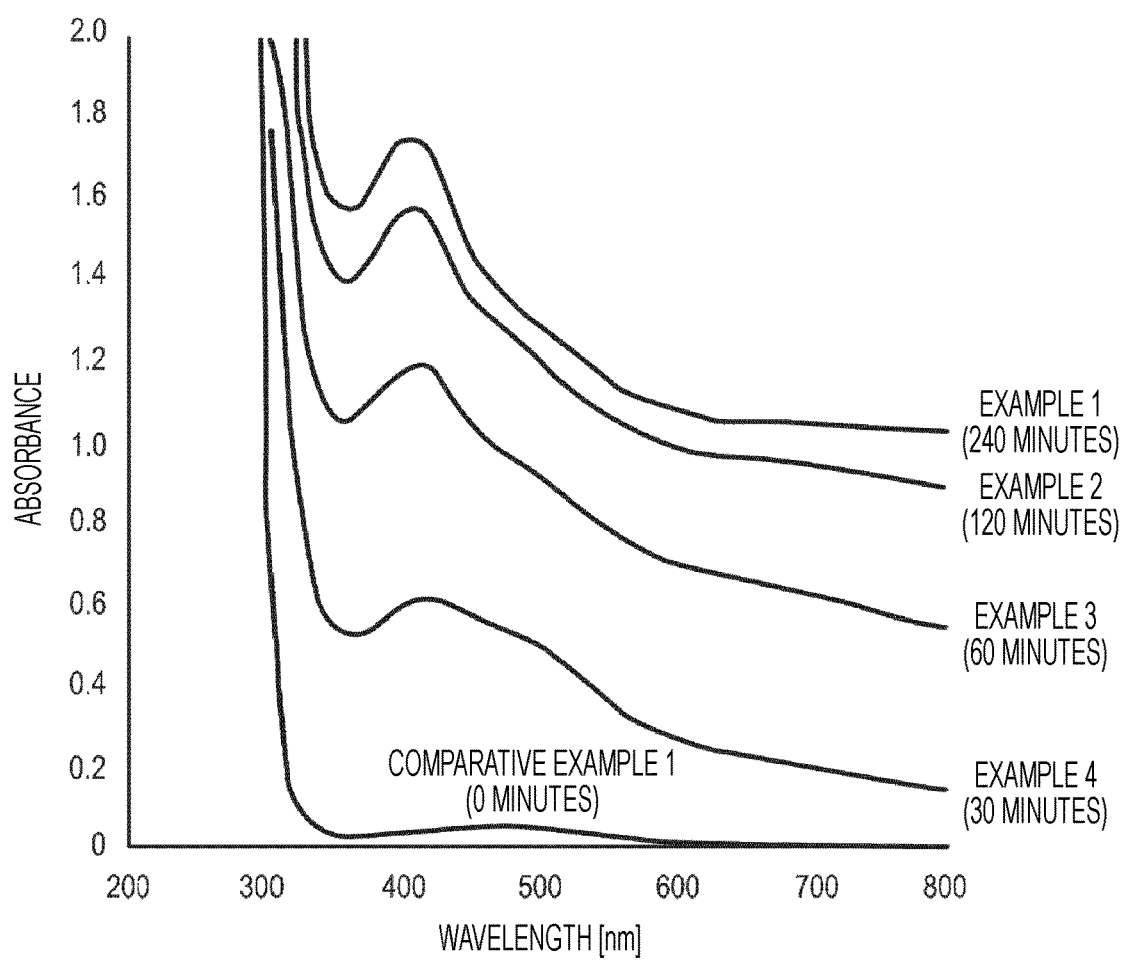
FIG. 8 is a graph showing formation of a dopamine polymer in Examples 1 to 4 and Comparative Example 1.

A constant amount of the DA/PBS solution 1 after taking out the retained hollow fiber membranes 1 to 4 was taken out, and the absorbance of the solution was measured by ultraviolet-visible spectroscopy (UV-vis) at a wavelength of 200 to 800 nm. FIG. 8 shows the results. In FIG. 8, high absorbance at 450 nm (abs.) is a barometer for the degree of polymerization of dopamine in the solution, indicating that the polymerization of dopamine is promoted by blowing oxygen (that is, dopamine is also polymerized on the surface of the hollow fiber membranes, and a dopamine layer is formed more quickly than in a comparative case where the hollow fiber membranes are left to stand in the atmosphere).

Comparative Example 1

Comparative coated hollow fiber membranes 1 were prepared in a similar manner to Examples 1 to 4 except that oxygen gas was not blown (that is, oxygen gas blowing time=0 min.)

That is, a DA/PBS solution 1 (pH 7.4) was prepared in a similar manner to Example 1 to 4.

Polypropylene porous hollow fiber membranes (outside diameter: 170 μm, inside diameter: 112 μm, thickness: 29 μm, pore size: 0.05 μm, porosity: 30 vol. %, membrane area: 0.05 m$^2$) were immersed in the prepared DA/PBS solution 1 to fill the lumina of the hollow fiber membranes with the DA/PBS solution 1. The status of the hollow fiber membranes were retained at 37° C. for one hour. Accordingly, dopamine was oxidized and polymerized to form a dopamine polymer layer (polymer layer) on the surface of the hollow fiber membranes (comparative retained hollow fiber membranes 1). The comparative retained hollow fiber membranes 1 were taken out from the DA/PBS solution 1, washed with RO water, and naturally dried at room temperature (25° C.) to obtain comparative coated hollow fiber membranes 1.

After taking out the comparative retained hollow fiber membranes 1, an amount of dopamine in the DA/PBS solution 1 was measured in a similar manner to Example 1 to 4. FIG. 8 shows the results.

Comparative Example 2

Dopamine hydrochloride (available from Sigma-Aldrich Japan) was added to a PBS solution (composition: 8 g/L NaCl, 0.2 g/L KCl, 1.15 g/L Na$_2$HPO$_4$, 0.2 g/L KH$_2$PO$_4$, pH 7.4) to prepare a DA/PBS solution 2 (pH 7.4) having a dopamine hydrochloride concentration of 2 mg/mL.

Polypropylene porous hollow fiber membranes (outside diameter: 170 μm, inside diameter: 112 μm, thickness: 29 μm, pore size: 0.05 μm, porosity: 30 vol. %, membrane area: 0.05 m$^2$) were immersed in the prepared DA/PBS solution 2 for 24 hours to fill the lumina of the hollow fiber membranes with the DA/PBS solution 2, and dopamine was oxidized and polymerized to form a dopamine polymer layer (polymer layer) on the surface of the hollow fiber membranes, thereby obtaining comparative coated hollow fiber membranes 2.

Figure 9:
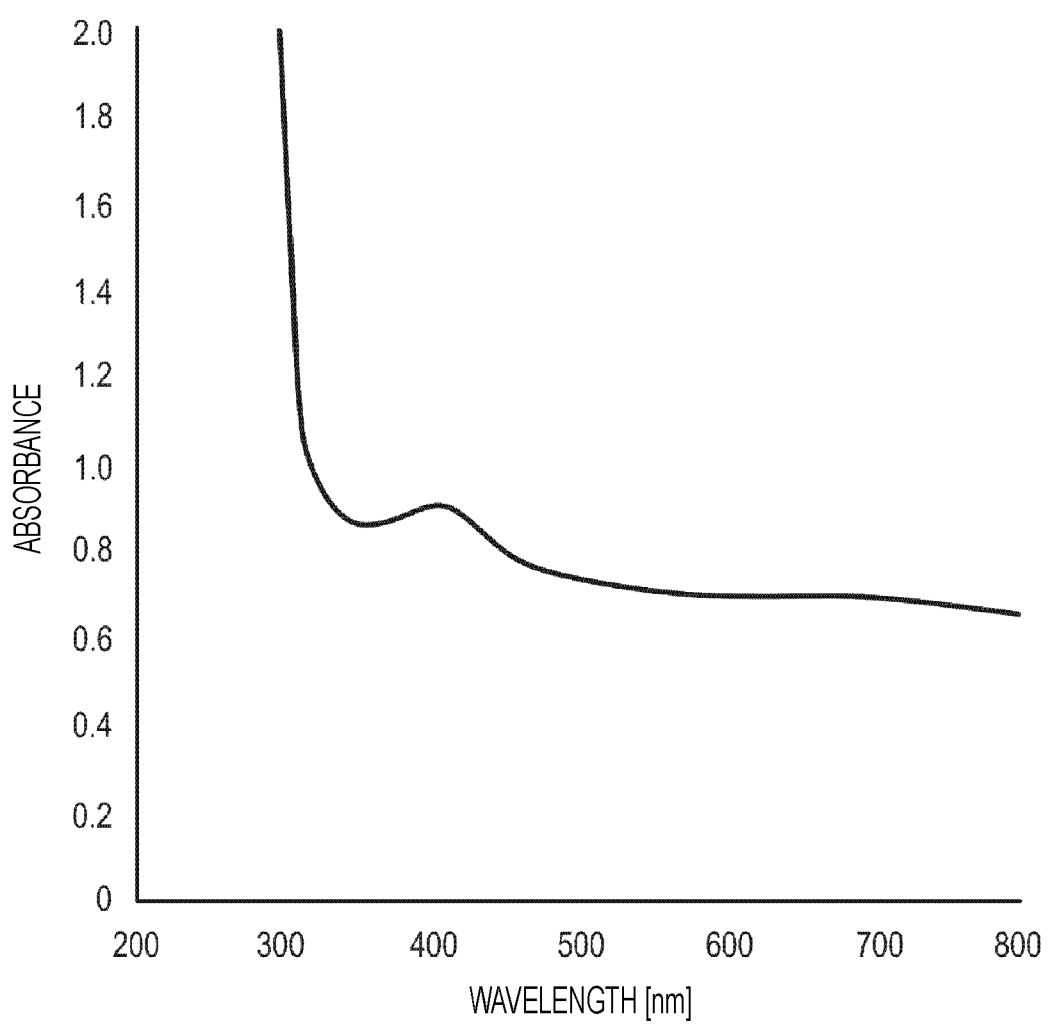
FIG. 9 is a graph showing formation of a dopamine polymer in Comparative Example 2.

After taking out comparative retained hollow fiber membranes 2 were taken out, an amount of dopamine in the DA/PBS solution 2 was measured in a similar manner to Example 1 to 4. FIG. 9 shows the results.

FIG. 8 shows that oxidation and polymerization of dopamine while blowing oxygen gas as in Examples 1-4 proceed polymerization of dopamine more efficiently than Comparative Example 1 with no blowing of oxygen gas. For this reason, when an antithrombotic drug layer containing an antithrombotic drug is formed on the dopamine polymer layer formed in Examples 1-4 herein, it is inferred that the antithrombotic drug layer comes in closer contact with the dopamine polymer layer than the dopamine polymer layer in Comparative Examples (therefore, it is possible to provide higher durability to an oxygenator).

In addition, a comparison between FIG. 8 and FIG. 9 shows that the method according to Examples 1-4 forms a comparable amount of dopamine polymer layer in less time.

Comparative Example 3

Polypropylene porous hollow fiber membranes (outside diameter: 170 μm, inside diameter: 112 μm, thickness: 29 μm, pore size: 0.05 μm, porosity: 30 vol. %, membrane area: 0.05 m$^2$) were prepared as uncoated hollow fiber membranes.

Evaluation

With regard to the coated hollow fiber membranes 3 obtained in Example 3, the comparative coated hollow fiber membranes 1 obtained in Comparative Example 1, and the uncoated hollow fiber membranes, gas permeability and anti-plasma leakage properties were evaluated.

Gas Permeability

Figure 10:
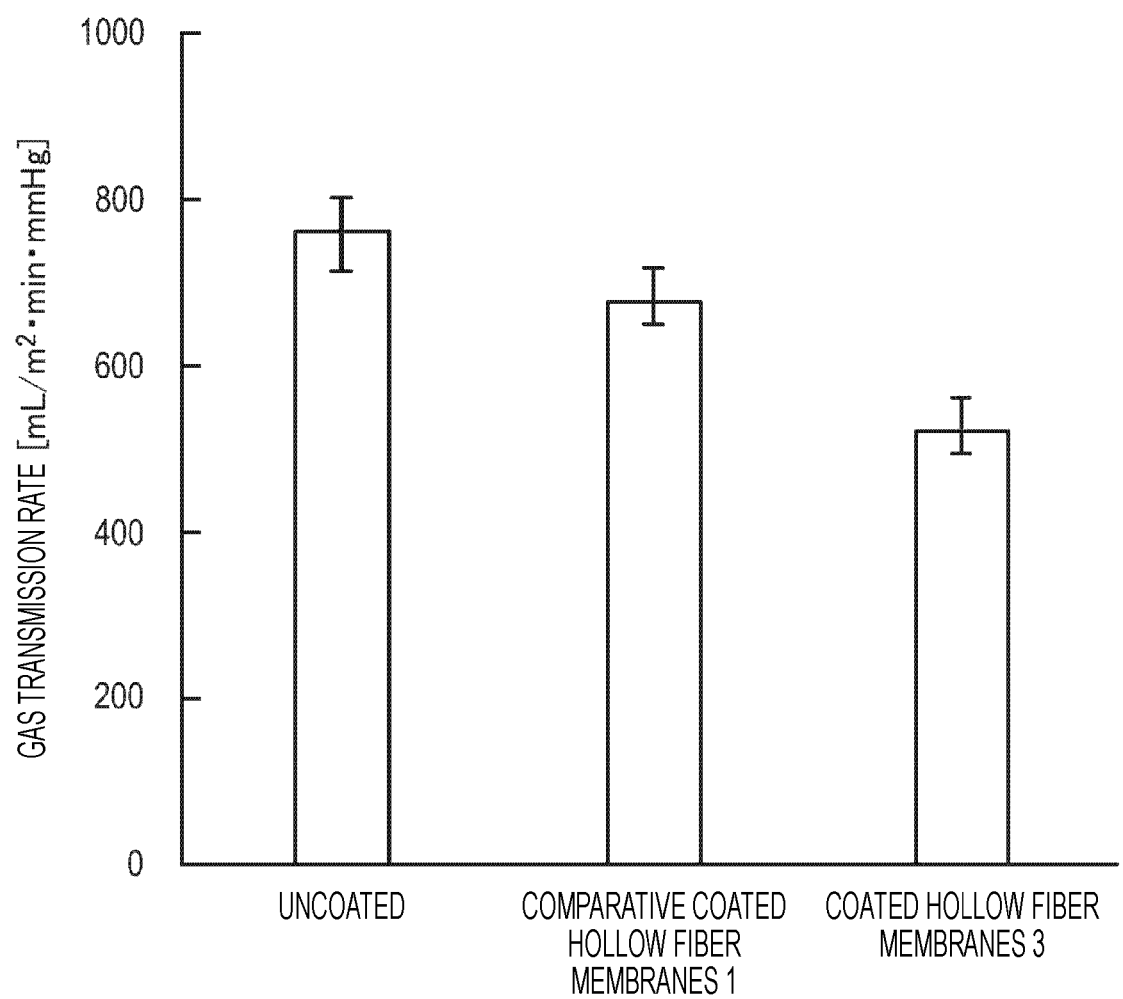
FIG. 10 is a graph illustrating gas permeability for coated and uncoated Examples.

The coated hollow fiber membranes 3 were potted in an epoxy resin, and the outside of the hollow fiber membranes 3 was filled with oxygen gas. A pressure of 50 mmHg was applied to the gas, and the rate of the gas flowing from the outside to the lumina of the hollow fiber membranes was measured to evaluate gas permeability. Gas permeability of the comparative coated hollow fiber membranes 1 and the uncoated hollow fiber membranes were also evaluated in a similar manner. FIG. 10 shows the results. FIG. 10 is a bar graph where the gas transmission rate (mL/m$^2$·min·mmHg) per unit (area·time) is taken along the ordinate. The larger the value of the ordinate, the better the gas permeability.

As illustrate in FIG. 10, the coated hollow fiber membranes 3 were found to be lower in gas permeability than the uncoated hollow fiber membranes (uncoated in FIG. 10) and the comparative coated hollow fiber membranes 1 but have sufficient gas permeability required for an oxygenator (1.0 mL/m$^2$·min·mmHg or more).

Anti-Plasma Leakage Properties

Figure 11:
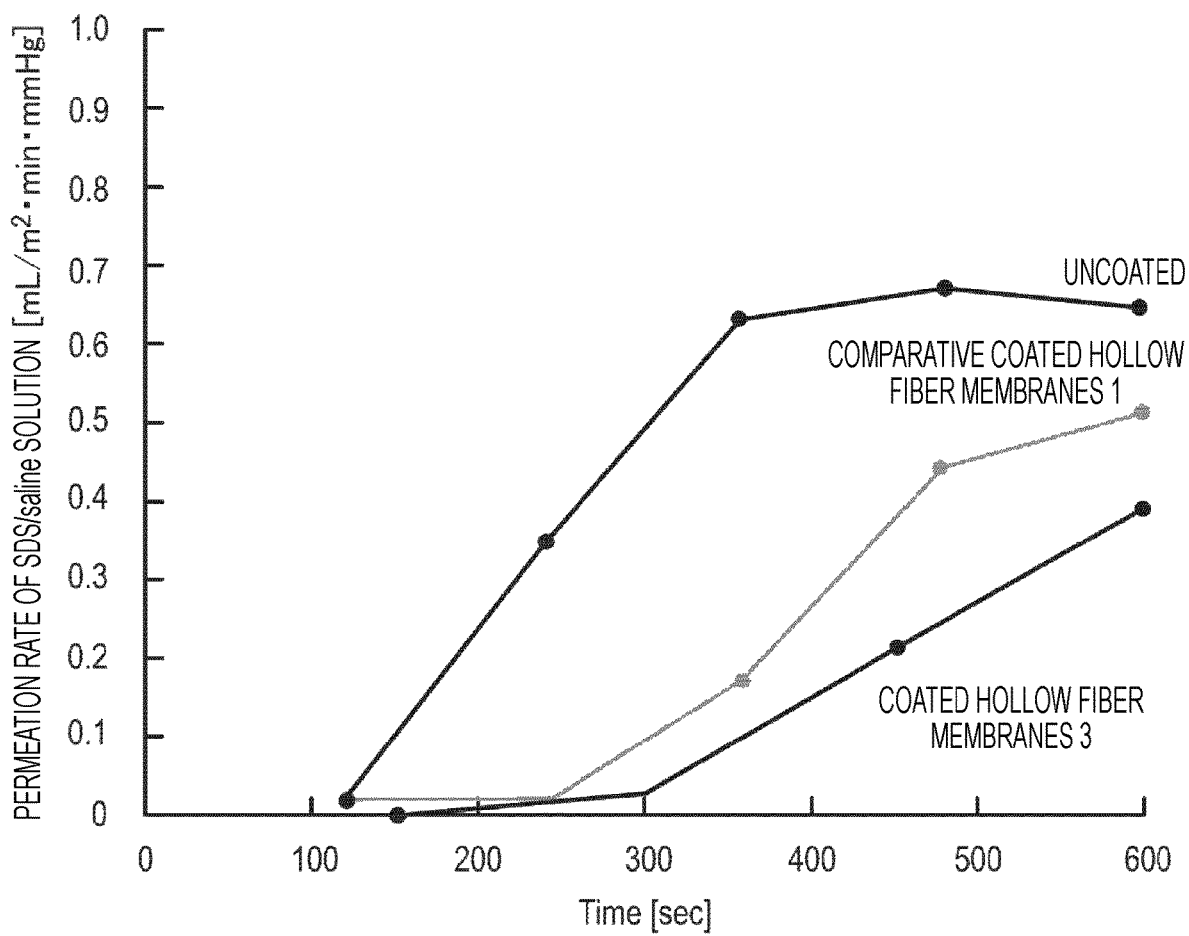
FIG. 11 is a graph illustrating anti-plasma leakage properties for coated and uncoated Examples.

The coated hollow fiber membranes 3 were potted in an epoxy resin, and the outside of the hollow fiber membranes 3 was filled with a solution (SDS/saline solution) having an SDS concentration of 1 mg/mL prepared by dissolving sodium dodecyl sulfate (SDS) in a 0.9 w/v % sodium chloride aqueous solution (saline solution). A pressure of 760 mmHg was applied to the SDS/saline solution, and the rate of the SDS/saline solution permeating the lumina from the outside of the hollow fiber membranes was measured to evaluate anti-plasma leakage properties. Anti-plasma leakage properties of the comparative coated hollow fiber membranes 1 and the uncoated hollow fiber membranes were also evaluated in a similar manner. FIG. 11 shows the results.

FIG. 11 is a graph where the permeation rate of the SDS/saline solution per unit (area·time) is taken along the ordinate and the time is taken along the abscissa. The larger the value of the ordinate, the better the anti-plasma leakage properties.

As illustrated in FIG. 11, the coated hollow fiber membranes 3 were found to have significantly improved anti-plasma leakage properties as compared with the uncoated hollow fiber membranes ("uncoated" in FIG. 11) and the comparative coated hollow fiber membranes 1.

What is claimed is:

1. A method for manufacturing an oxygenator having a plurality of porous hollow fiber membranes for gas exchange comprised of polypropylene, wherein each hollow fiber membrane has an inner surface that forms a lumen and an outer surface, wherein the method comprises the steps of:
preparing a coating solution containing at least one compound selected from the group consisting of dopamine, salt of dopamine, and oligomer of dopamine; and
bringing the inner surface or the outer surface of the hollow fiber membranes into contact with the coating solution for less than ten hours while blowing oxygen gas in the coating solution to form a dopamine polymer layer containing a polymer of the compound on the inner surface or the outer surface.

2. The method according to claim 1, wherein the compound is dopamine or a salt of dopamine.

3. The method according to claim 1, wherein the dopamine polymer layer is formed on the outer surface of the hollow fiber membranes, and wherein the method further comprises the step of:
forming an antithrombotic drug layer having an antithrombotic drug on the dopamine polymer layer.

4. The method according to claim 3, wherein the antithrombotic drug is a compound having a unit (1) represented by the Formula (1):

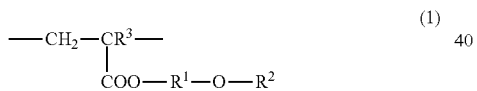

where $R^1$ is a $C_{1-4}$ alkylene group; $R^2$ is a $C_{1-4}$ alkyl group; and $R^3$ is a hydrogen atom or a methyl group.

5. The method according to claim 1 wherein the step of bringing the inner surface or the outer surface of the hollow fiber membranes into contact with the coating solution while blowing oxygen gas in the coating solution is performed for more than fifteen minutes.

6. The method according to claim 1 wherein the step of bringing the inner surface or the outer surface of the hollow fiber membranes into contact with the coating solution while blowing oxygen gas in the coating solution is performed for more than thirty minutes and less than eight hours.

7. The method according to claim 1 wherein the step of bringing the inner surface or the outer surface of the hollow fiber membranes into contact with the coating solution while blowing oxygen gas in the coating solution is performed for more than one hour and less than 5 hours.

8. The method according to claim 1 wherein the step of bringing the inner surface or the outer surface of the hollow fiber membranes into contact with the coating solution while blowing oxygen gas in the coating solution is performed for more than two hours and less than four hours.

9. The method according to claim 1 wherein the step of bringing the inner surface or the outer surface of the hollow fiber membranes into contact with the coating solution while blowing oxygen gas in the coating solution is performed for a time sufficient to produce a dopamine polymer layer having a thickness from 10 to 500 nm.

10. The method according to claim 1 wherein the step of bringing the inner surface or the outer surface of the hollow fiber membranes into contact with the coating solution while blowing oxygen gas in the coating solution is performed for a time sufficient to produce a dopamine polymer layer having a thickness from 150 to 300 nm.

11. An oxygenator for treating blood, comprising:
a plurality of porous hollow fiber membranes for gas exchange each of which has an inner surface and an outer surface; and
a housing which directs the blood to one of the inner surfaces or the outer surfaces and which directs a gas to the other one of the inner surfaces or the outer surfaces;
wherein the inner surfaces or the outer surfaces which receive the blood are provided with a dopamine polymer layer which is formed by (1) preparing a coating solution containing at least one compound selected from the group consisting of dopamine, salt of dopamine, and oligomer of dopamine, and (2) bringing the hollow fiber membranes into contact with the coating solution for less than ten hours while blowing oxygen gas in the coating solution.

12. The oxygenator of claim 11 wherein the compound is dopamine or a salt of dopamine.

13. The oxygenator according to claim 11, wherein the dopamine polymer layer is formed on the outer surface of the hollow fiber membranes, and wherein the oxygenator further comprises an antithrombotic drug layer having an antithrombotic drug on the dopamine polymer layer.

14. The oxygenator according to claim 13, wherein the antithrombotic drug is a compound having a unit (1) represented by the Formula (1):

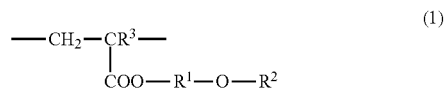

where $R^1$ is a $C_{1-4}$ alkylene group; $R^2$ is a $C_{1-4}$ alkyl group; and $R^3$ is a hydrogen atom or a methyl group.

15. The oxygenator according to claim 11 wherein the dopamine polymer layer is formed by bringing the inner surface or the outer surface of the hollow fiber membranes into contact with the coating solution while blowing oxygen gas in the coating solution for more than fifteen minutes.

16. The oxygenator according to claim 11 wherein the dopamine polymer layer is formed by bringing the inner surface or the outer surface of the hollow fiber membranes into contact with the coating solution while blowing oxygen gas in the coating solution for more than thirty minutes and less than eight hours.

17. The oxygenator according to claim 11 wherein the dopamine polymer layer is formed by bringing the inner surface or the outer surface of the hollow fiber membranes into contact with the coating solution while blowing oxygen gas in the coating solution for more than one hour and less than 5 hours.

18. The oxygenator according to claim 11 wherein the dopamine polymer layer is formed by bringing the inner surface or the outer surface of the hollow fiber membranes into contact with the coating solution while blowing oxygen gas in the coating solution for more than two hours and less than four hours.

19. The oxygenator according to claim 11 wherein the dopamine polymer layer is formed by bringing the inner surface or the outer surface of the hollow fiber membranes into contact with the coating solution while blowing oxygen gas in the coating solution for a time sufficient to produce a dopamine polymer layer having a thickness from 10 to 500 nm.

20. The oxygenator according to claim 11 wherein the dopamine polymer layer is formed by bringing the inner surface or the outer surface of the hollow fiber membranes into contact with the coating solution while blowing oxygen gas in the coating solution for a time sufficient to produce a dopamine polymer layer having a thickness from 150 to 300 nm.

* * * * *